(12) United States Patent
Merchant et al.

(10) Patent No.: US 7,794,466 B2
(45) Date of Patent: Sep. 14, 2010

(54) METHOD AND APPARATUS FOR PERFORMING MULTIDIRECTIONAL TIBIAL TUBERCLE TRANSFERS

(75) Inventors: Alan C. Merchant, 124 Marvin Ave., Los Altos, CA (US) 94022; Kelly G. Ammann, Boulder, CO (US); Raymond A. Sirianne, Evergreen, CO (US)

(73) Assignee: Alan C. Merchant, Los Altos, CA (US)

( * ) Notice: Subject to any disclaimer, the term of this patent is extended or adjusted under 35 U.S.C. 154(b) by 769 days.

(21) Appl. No.: 11/788,318

(22) Filed: Apr. 19, 2007

(65) Prior Publication Data
US 2008/0154267 A1 Jun. 26, 2008

Related U.S. Application Data

(60) Provisional application No. 60/793,120, filed on Apr. 19, 2006, provisional application No. 60/847,501, filed on Sep. 27, 2006.

(51) Int. Cl.
*A61B 17/58* (2006.01)
(52) U.S. Cl. .................. 606/87; 606/86 R
(58) Field of Classification Search ............ 606/87, 606/86 R, 79, 88, 89, 96, 102, 179, 170, 180; 128/898
See application file for complete search history.

(56) References Cited

U.S. PATENT DOCUMENTS

| | | | | |
|---|---|---|---|---|
| 5,620,448 A * | 4/1997 | Puddu | .......................... | 606/87 |
| 6,008,433 A * | 12/1999 | Stone | ....................... | 623/20.14 |
| 6,086,593 A * | 7/2000 | Bonutti | ....................... | 606/87 |
| 6,203,546 B1 * | 3/2001 | MacMahon | ................... | 606/87 |
| 6,689,139 B2 * | 2/2004 | Horn | ........................... | 606/87 |
| 6,796,986 B2 * | 9/2004 | Duffner | ....................... | 606/87 |
| 6,823,871 B2 | 11/2004 | Schmieding | | |

* cited by examiner

*Primary Examiner*—Pedro Philogene
(74) *Attorney, Agent, or Firm*—Pandiscio & Pandiscio

(57) ABSTRACT

A method and apparatus for performing a multidirectional tibial tubercle transfer, comprising: positioning a jig against the anterior portion of the tibia, the jig comprising first and second cutting guides which simultaneously converge towards one another as they extend distally down the tibia and posteriorly towards the tibia; cutting first and second saw cuts into the tibia; attaching an extender to the jig, wherein the extender comprises a third cutting guide which simultaneously converges towards the first cutting guide as the third cutting guide extends distally down the tibia and posteriorly towards the tibia; cutting a third saw cut into the tibia; freeing a first and second bone block from the tibia; freeing a second bone block from the tibia; and transferring the position of the first bone block relative to the tibia.

27 Claims, 44 Drawing Sheets

METHOD AND APPARATUS FOR PERFORMING MULTIDIRECTIONAL TIBIAL TUBERCLE TRANSFERS

REFERENCE TO PENDING PRIOR PATENT APPLICATIONS

This patent application claims benefit of:

(1) pending prior U.S. Provisional Patent Application Ser. No. 60/793,120, filed Apr. 19, 2006 by Alan C. Merchant for JIGS & INSTRUMENTATION FOR PERFORMING MULTIDIRECTIONAL TIBIAL TUBERCLE TRANSFERS; and (2) pending prior U.S. Provisional Patent Application Ser. No. 60/847,501, filed Sep. 27, 2006 by Alan C. Merchant et al. for METHOD FOR PERFORMING A TIBIAL TUBERCLE TRANSFER.

The two (2) above-identified patent applications are hereby incorporated herein by reference.

FIELD OF THE INVENTION

This invention relates to surgical methods and apparatus in general, and more particularly to surgical methods and apparatus for performing tibial tubercle transfers.

BACKGROUND OF THE INVENTION

In the field of orthopedic surgery, transferring the tibial tubercle is a well-recognized operative technique to correct the alignment of the extensor mechanism of the knee when that portion of the knee is found to be misaligned. This is traditionally done by moving the tibial tubercle from its current, non-optimum location to a more desirable location. The most common directions of transfer are medial and anteromedial, although other directions have been described in the literature as well.

Prior art approaches for transferring the tibial tubercle have generally proven to be problematic for a variety of reasons. Among other things, prior art approaches for transferring the tibial tubercle have generally proven to be (i) relatively complex and time-consuming to perform, (ii) less precise than desired, (iii) not highly reproducible from patient-to-patient and surgeon-to-surgeon, (iv) technique restrictive, and/or (v) procedurally invasive.

Thus, there is a need for an improved method and apparatus for transferring the tibial tubercle, such that the transfer process is simpler and faster to perform, more precise, more highly reproducible from patient to patient and surgeon to surgeon, less technique restrictive, and/or less invasive than prior art techniques.

SUMMARY OF THE INVENTION

These and other objects are addressed by the present invention, which comprises an improved method and apparatus for transferring the tibial tubercle.

More particularly, in one form of the invention, there is provided a method for performing a multidirectional tibial tubercle transfer, comprising:

positioning a jig against the anterior portion of the tibia, the jig comprising first and second cutting guides, wherein the first and second cutting guides simultaneously converge towards one another as they extend (i) distally down the tibia, and (ii) posteriorly towards the tibia;

cutting first and second saw cuts into the tibia, wherein the first saw cut is aligned with the first cutting guide and the second saw cut is aligned with the second cutting guide;

attaching an extender to the jig, wherein the extender comprises a third cutting guide, wherein the third cutting guide simultaneously converges towards the first cutting guide as the third cutting guide extends (i) distally down the tibia, and (ii) posteriorly towards the tibia;

cutting a third saw cut into the tibia, wherein the third saw cut is aligned with the third cutting guide;

freeing a first bone block from the tibia, wherein the first bone block is formed between the first saw cut and the second saw cut, and freeing a second bone block from the tibia, wherein the second bone block is formed between the first saw cut and the third saw cut; and transferring the position of the first bone block relative to the tibia.

In another form of the invention there is provided apparatus for performing a multidirectional tibial tubercle transfer, comprising:

a jig for positioning against the anterior portion of the tibia, the jig comprising first and second cutting guides, wherein the first and second cutting guides simultaneously converge towards one another as they extend (i) distally down the tibia, and (ii) posteriorly towards the tibia; and an extender for attaching to the jig, wherein the extender comprises a third cutting guide, wherein the third cutting guide simultaneously converges towards the first cutting guide as the third cutting guide extends (i) distally down the tibia, and (ii) posteriorly towards the tibia.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like elements and further wherein.

DETAILED DESCRIPTION OF THE PREFERRED EMBODIMENTS

Tibial Tubercle Transfer Procedure in General

The present invention comprises an improved method and apparatus for transferring the tibial tubercle. For clarity of explanation, the present invention will hereinafter be discussed in the context of a medial transfer, although it will be appreciated that other transfer directions are also possible.

Figure 1:
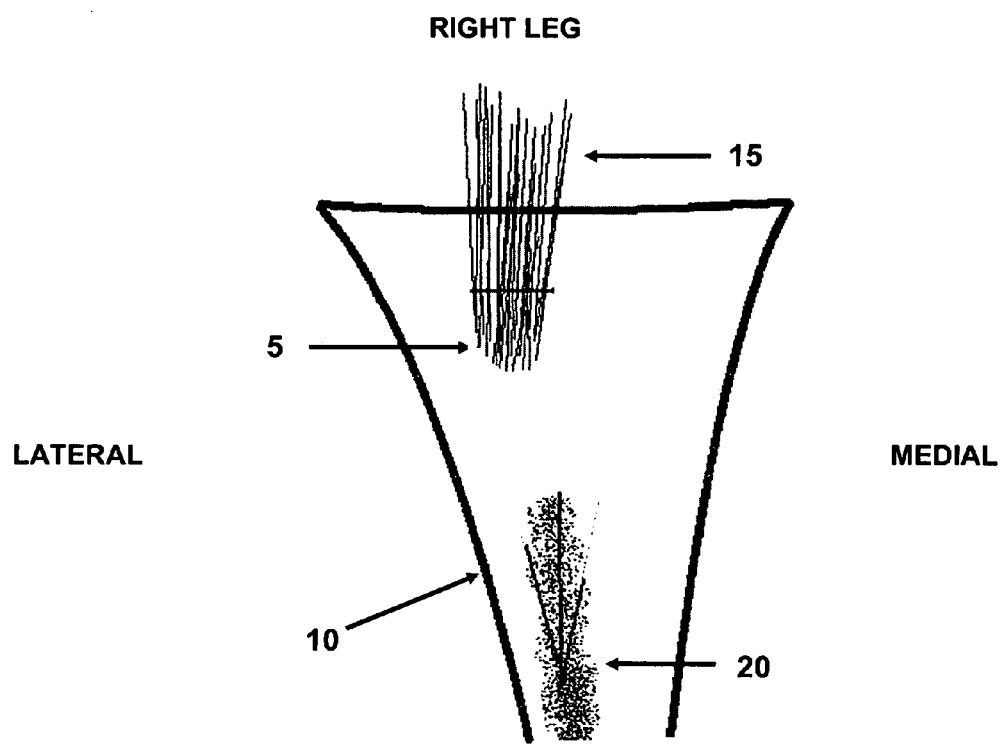
FIGS. 1-21 are a series of schematic views illustrating the tibial tubercle transfer procedure in general.
Figure 2:
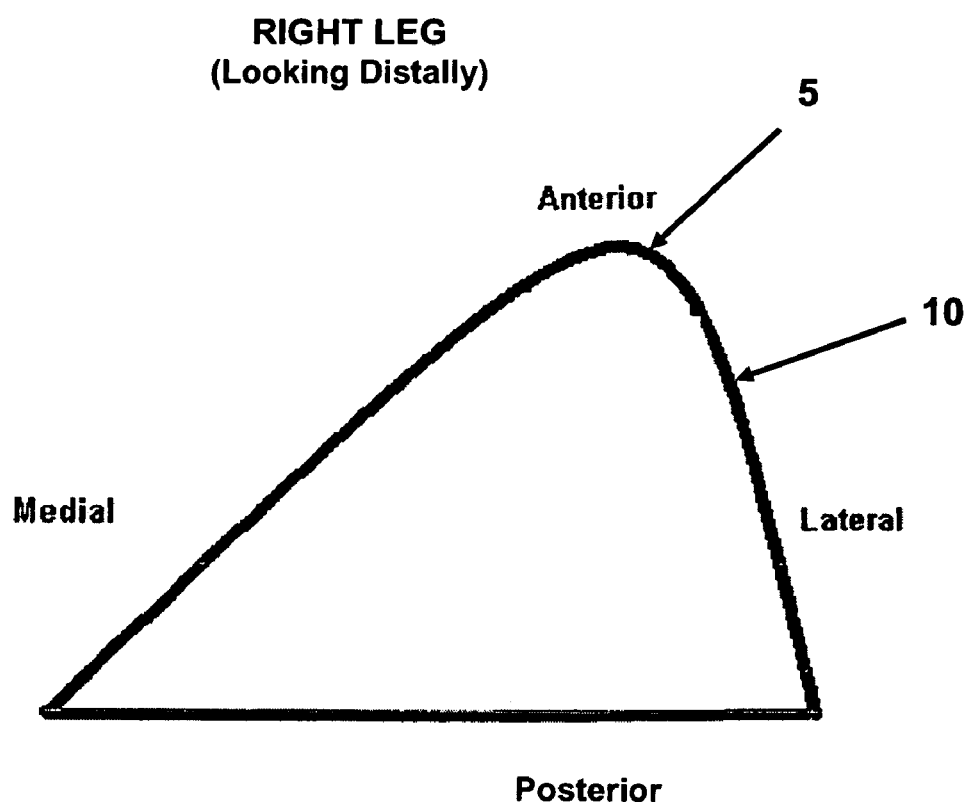

More particularly, and looking now at FIGS. 1 and 2, the tibial tubercle 5 of tibia 10 is first exposed through a small incision in the skin (not shown). Note how the insertion point of patella tendon 15 into tibial tubercle 5 lies above (i.e., proximal to) the tibial crest 20 of tibia 10.

Figure 3:
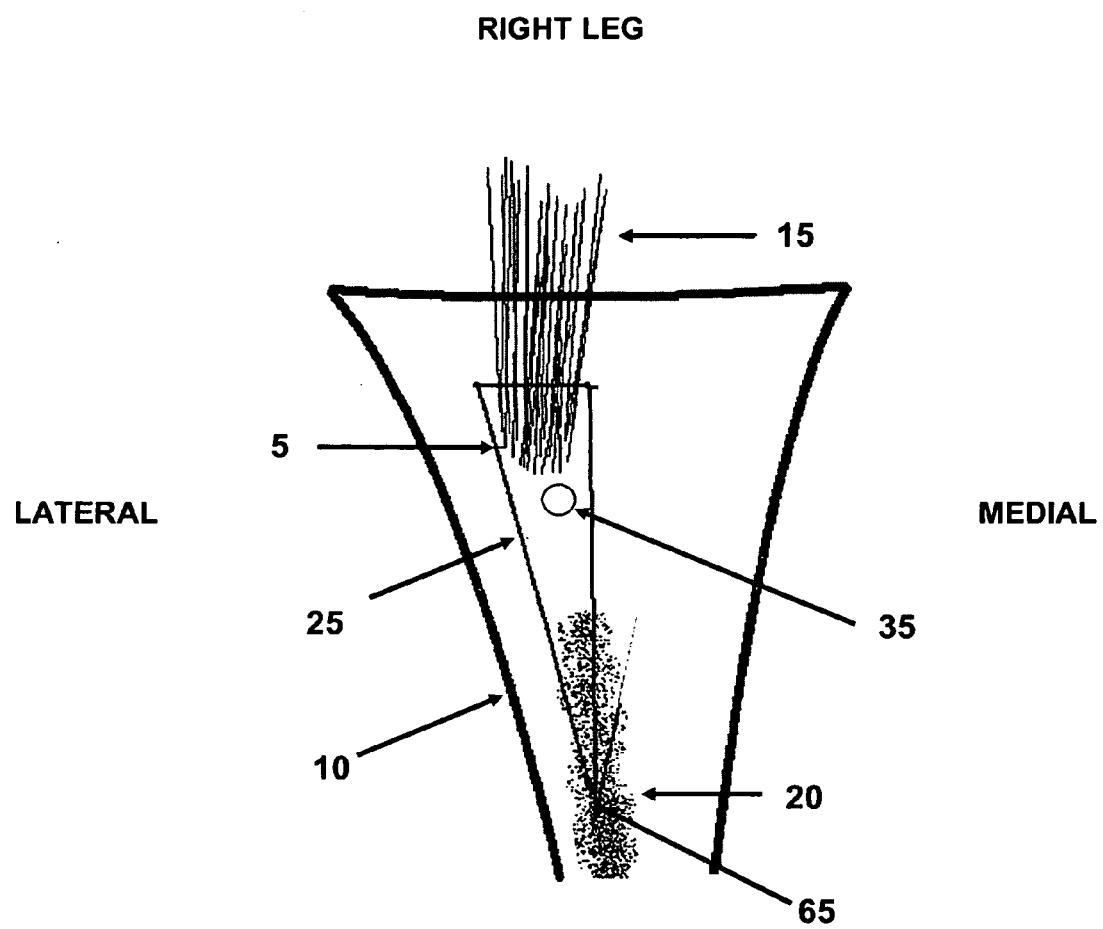
Figure 4:
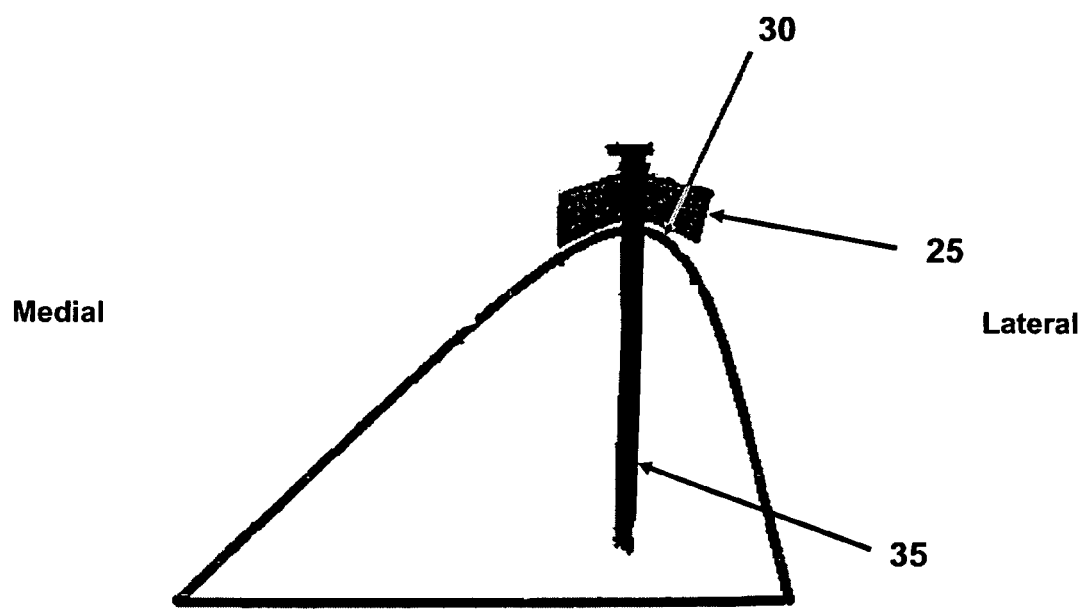
Figure 5:
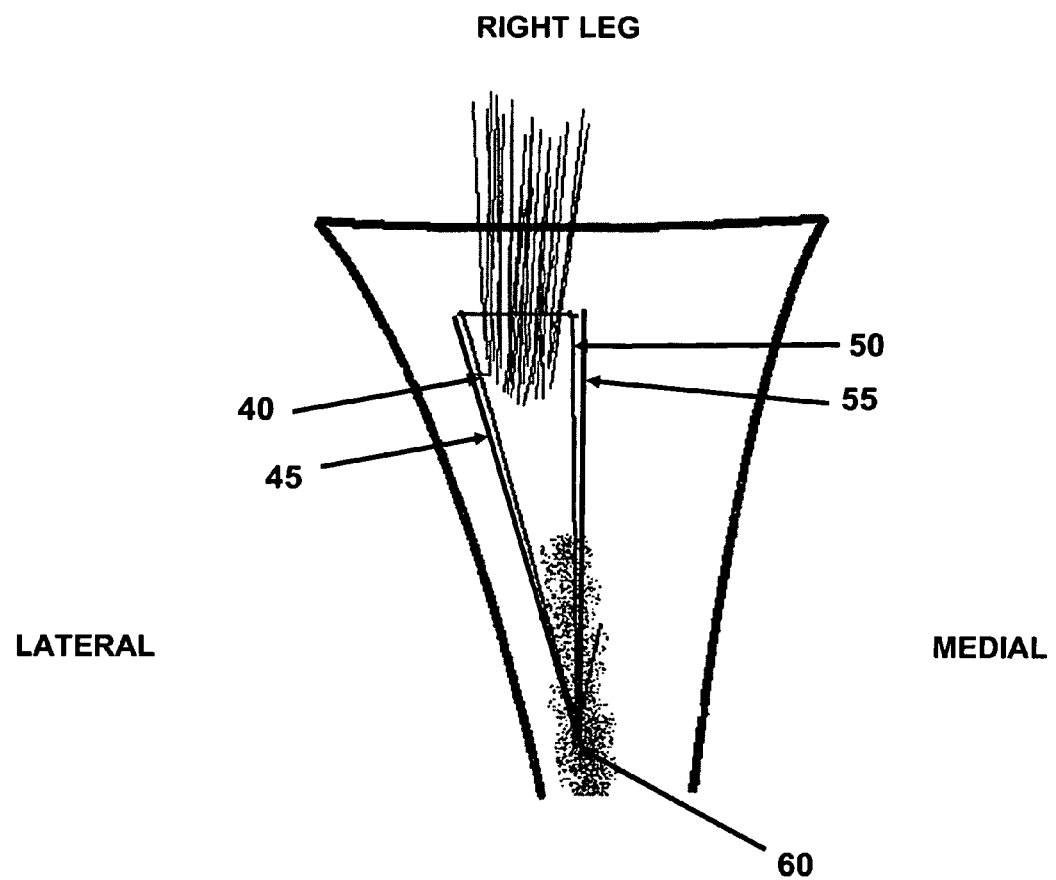

Next, and looking now at FIGS. 3 and 4, an appropriately-sized jig 25 is selected to fit onto tibial tubercle 5. Jig 25 is selected so as to be sized proportional to the size of the portion of the tibial tubercle which is to be transferred. To this end, the surgeon is preferably provided with a surgical kit comprising a plurality of various-sized jigs for use with the tibial tubercle transfer procedure of the present invention. This allows the surgeon to select the appropriate jig for use in a particular patient's procedure. Jig 25 is aligned onto the anterior surface 30 of tibial tubercle 5 and fixed in place with one or more bone screws 35. Then the body of jig 25 is used to guide a saw cut on either side of the jig, with the body of the jig being configured so that (i) the saw cuts taper to a point distally, and (ii) the saw cuts taper posteriorly.

Figure 6:
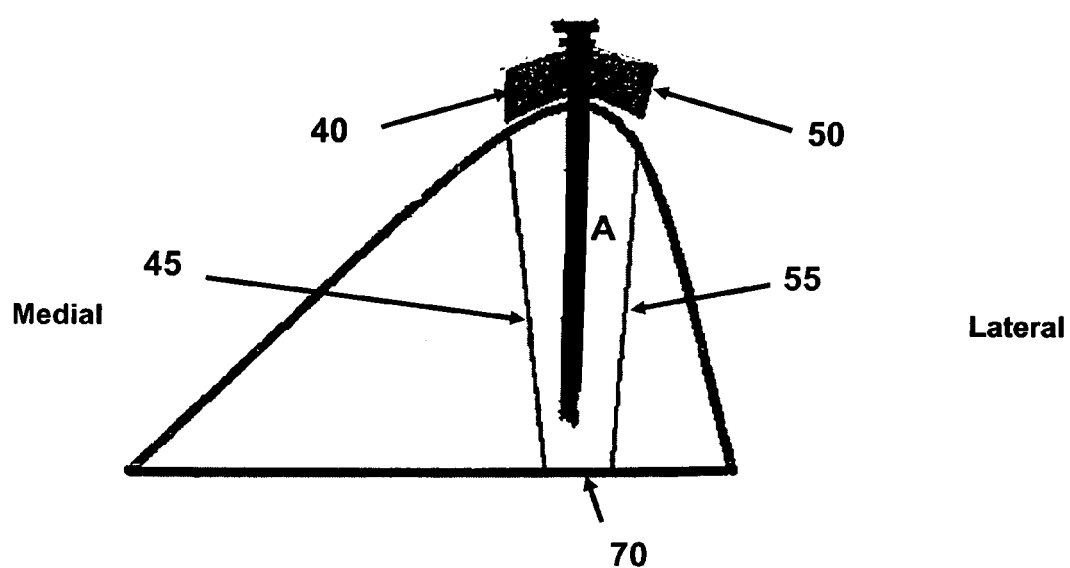

More particularly, and looking now at FIGS. 3-6, a surface 40 on the lateral side of jig 25 is used to guide a saw cut 45 into tibia 10, and another surface 50 on the medial side of jig 25 is used to guide a saw cut 55 into tibia 10. Note how saw cuts 45 and 55 simultaneously converge toward one another as they extend (i) distally down tibia 10 (FIG. 5), meeting at a point 60 at the distal tip 65 of jig 25, and (ii) posteriorly into tibia 10 (FIG. 6). Saw cuts 45 and 55 are completed to the posterior cortex using thin non-tapered osteotomes of the sort known in the art (not shown). The degree of convergence of saw cuts 45 and 55, in the anterior-posterior sense, is such that the two saw cuts do not meet before they encounter the posterior cortex, i.e., a face 70 (FIG. 6) of bone is demarcated between the saw cuts 45 and 55 where they open on the posterior cortex.

Figure 7:
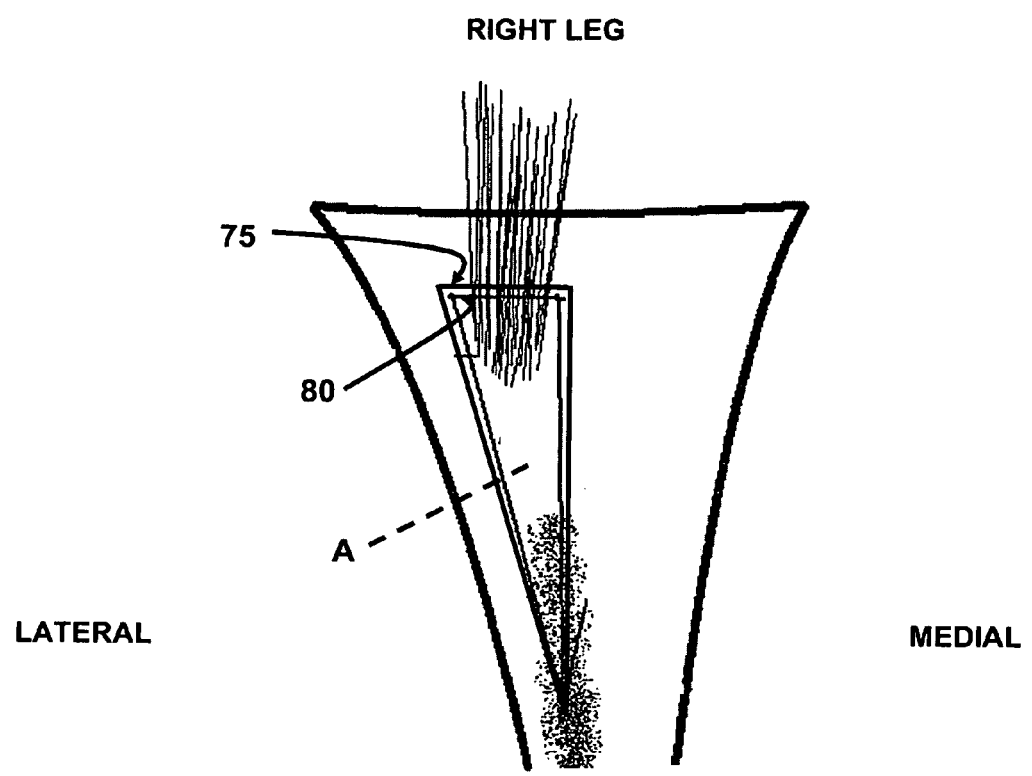

Next, and looking now at FIG. 7, a third saw cut 75 is made, anterior-to-posterior and perpendicular to the longitudinal axis of tibia 10, using non-tapered osteotomes, just at the proximal attachment point ("insertion point") of the patellar tendon. If desired, a surface 80 on jig 25 can be used to guide placement of saw cut 75. In one form of the present invention, saw cut 75 is made beneath the patellar tendon 15 and superior to the point where the patellar tendon inserts into tibia 10, with care being taken not to damage the patellar tendon. In another form of the present invention, saw cut 75 is made through the patellar tendon: in this case, the patellar tendon is restored at the conclusion of the procedure, e.g., by suturing. Saw cut 75 extends from the anterior side of tibia 10 to the posterior cortex.

It should be noted that the degree of displacement of saw cut 55 from saw cut 45 is directly proportional to the amount of the tibial tubercle which is to be transferred during the procedure.

At this point, and looking now at FIGS. 6 and 7, a wedge of bone A has been freed from tibia 10. This wedge of bone A will include the point where patellar tendon 15 inserts onto tibia 10.

Figure 8:
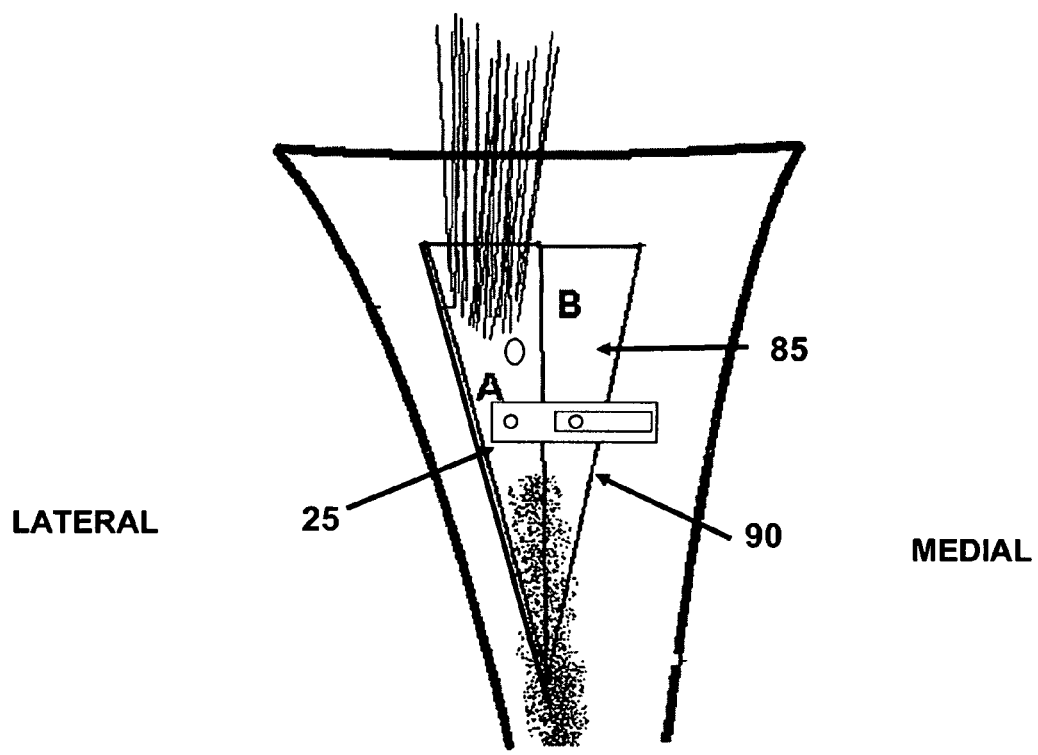
Figure 9:
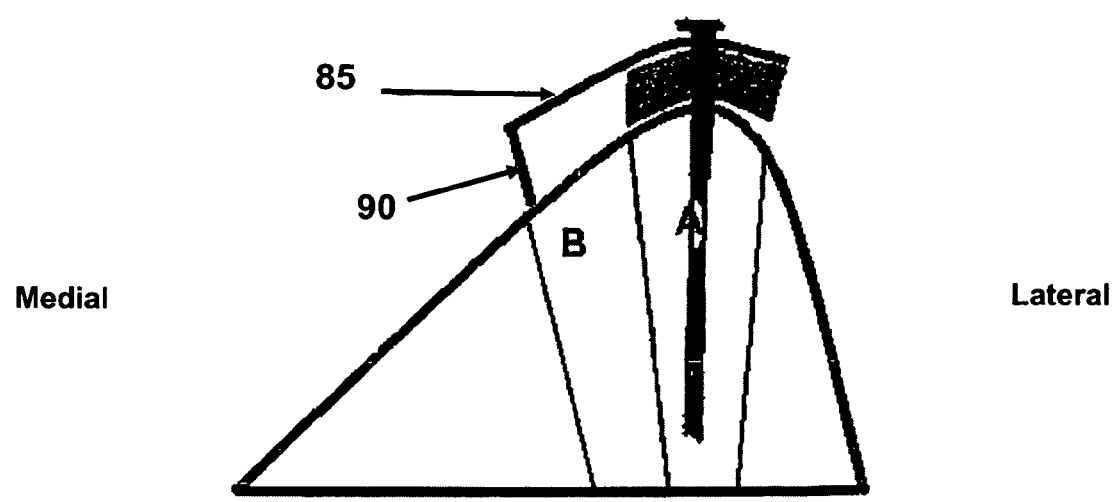
Figure 10:
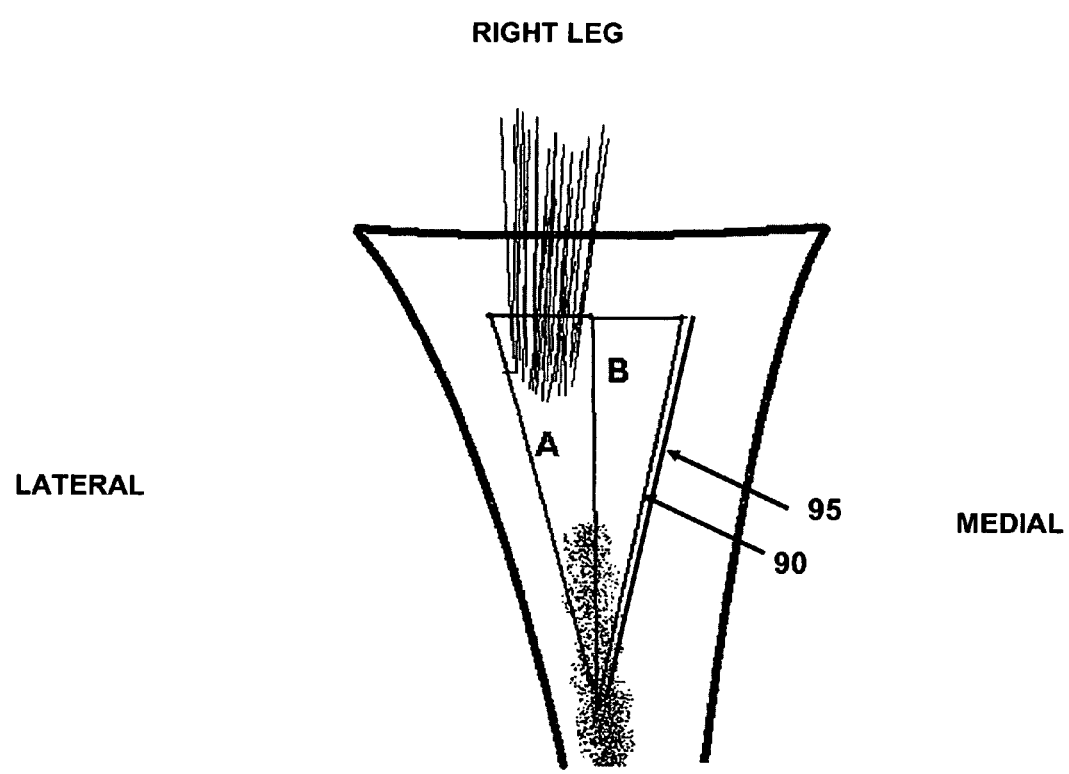
Figure 11:
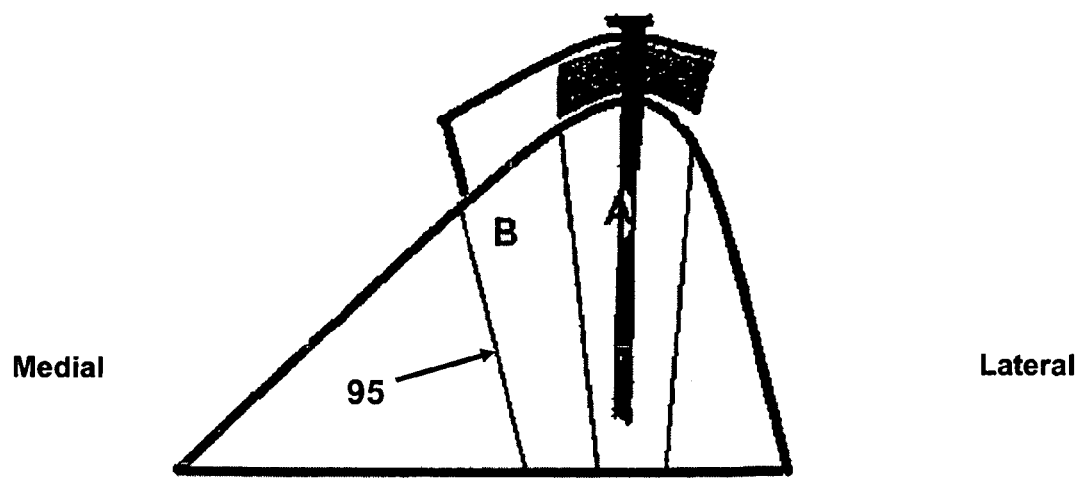

Next, and looking now at FIGS. 8 and 9, an adjustable sidearm 85 is affixed to jig 25. Adjustable sidearm 85 includes a flat saw guide 90 which is angled distally and posteriorly so that it can be used to establish a saw cut that will meet the two previous saw cuts 45 and 55 at the distal point 60. More particularly, sidearm 85 is adjusted relative to jig 25 so that the sidearm's flat saw guide 90 is set to the precise distance that the tibial tubercle is to be moved medially, and then sidearm 85 is locked in place. Then a fourth saw cut 95 is made along flat saw guide 90. Due to the disposition of flat saw guide 90, and as seen in FIGS. 10 and 11, (i) saw cut 95 tapers distally so as to meet the two previous saw cuts 45 and 55 at the distal point 60, and (ii) saw cut 95 tapers posteriorly into tibia 10. Fourth saw cut 95 is completed with non-tapered osteotomes so that it opens on the posterior cortex.

It should be noted that the degree of displacement of saw cut 95 from saw cut 55 is directly proportional to the distance which the tibial tubercle is to be moved during the procedure.

Figure 12:
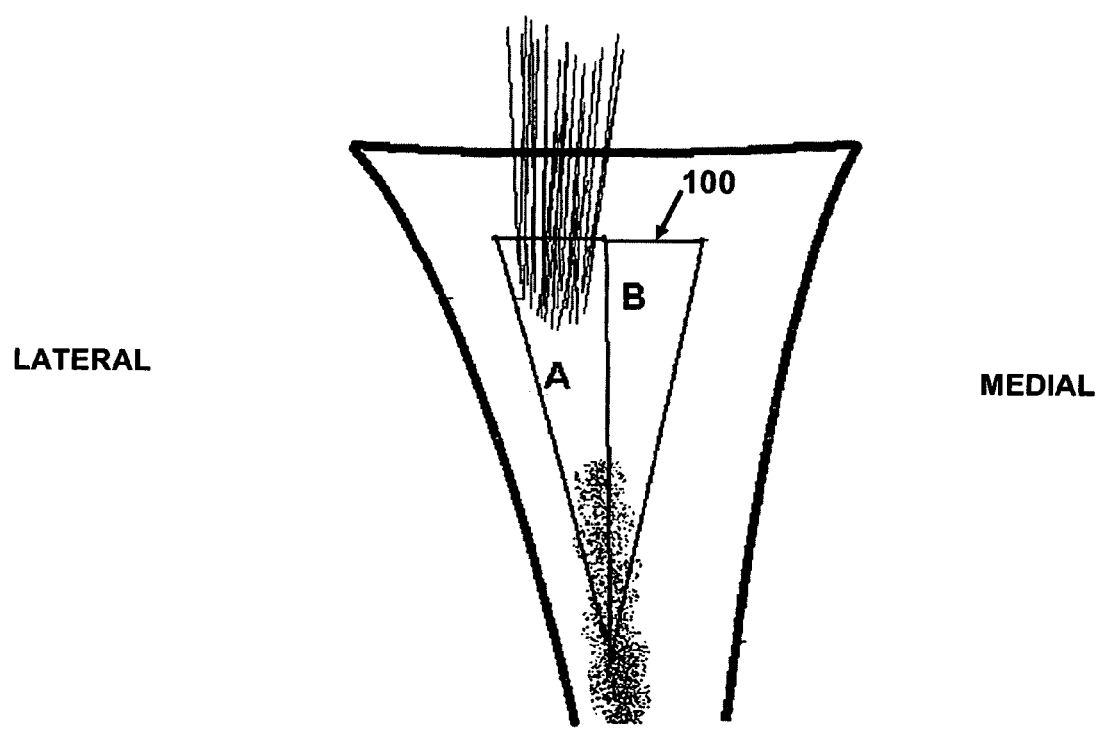

Next, as shown in FIG. 12, the transverse proximal cut 75 is extended medially at 100, thus creating a second wedge of bone B. Then jig 25 and adjustable sidearm 85 are removed.

Figure 13:
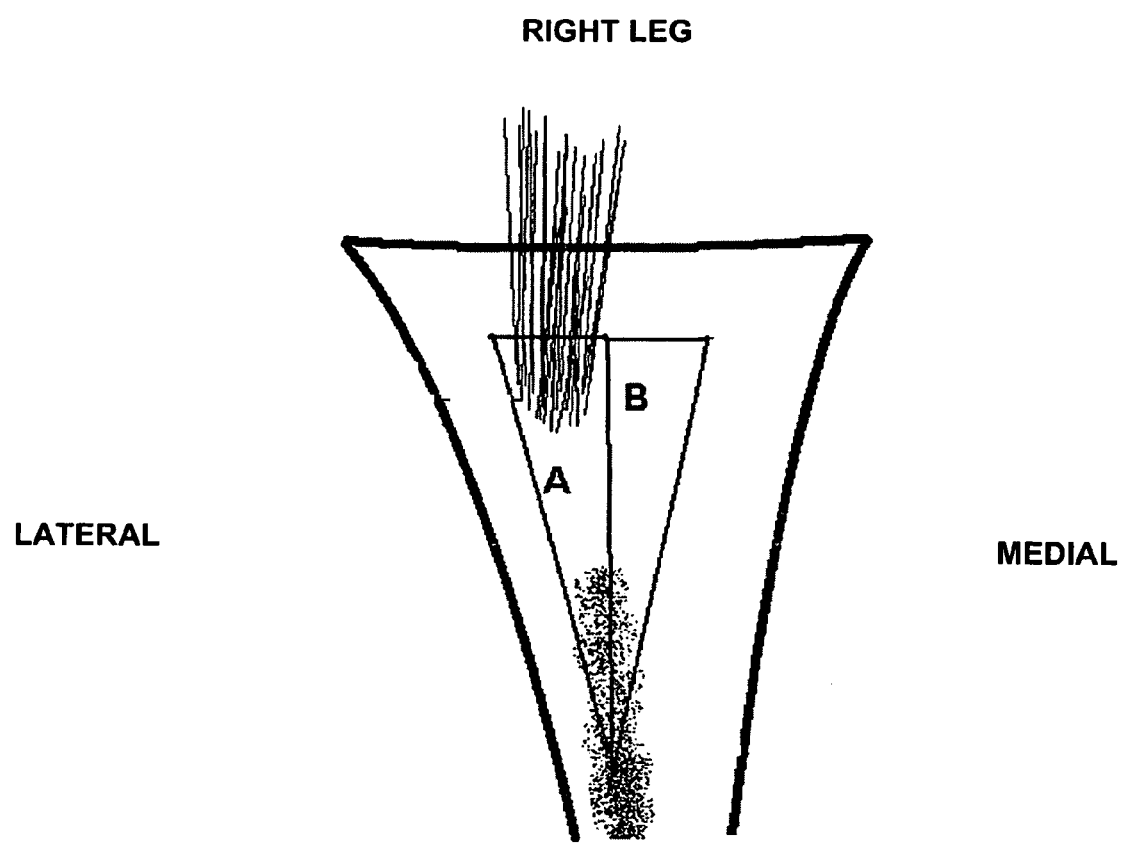
Figure 14:
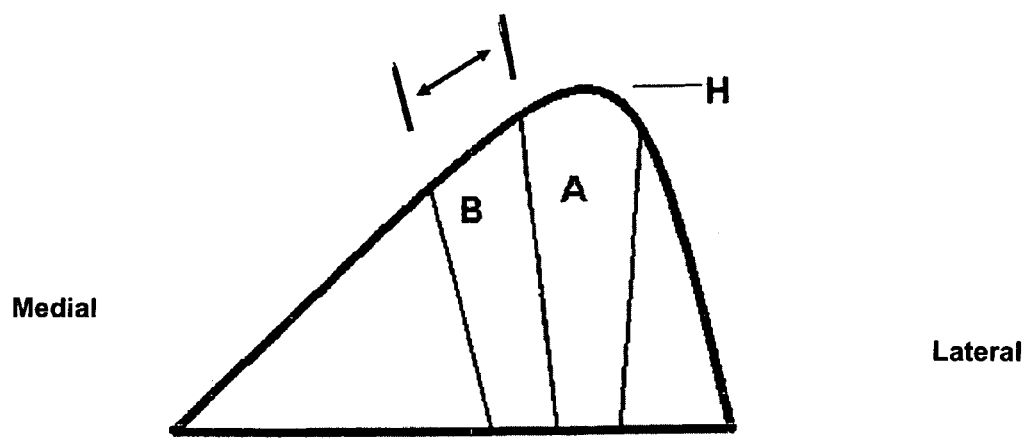
Figure 15:
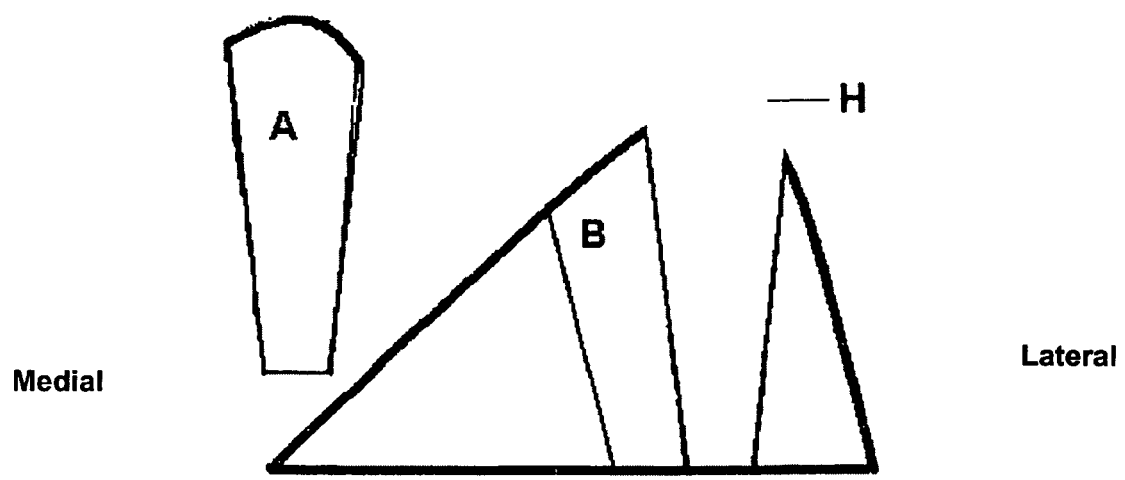
Figure 16:
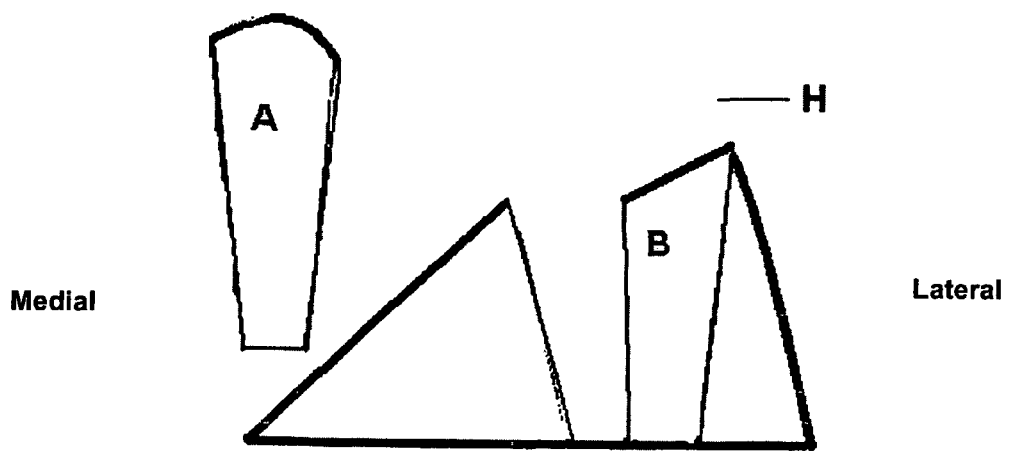
Figure 17:
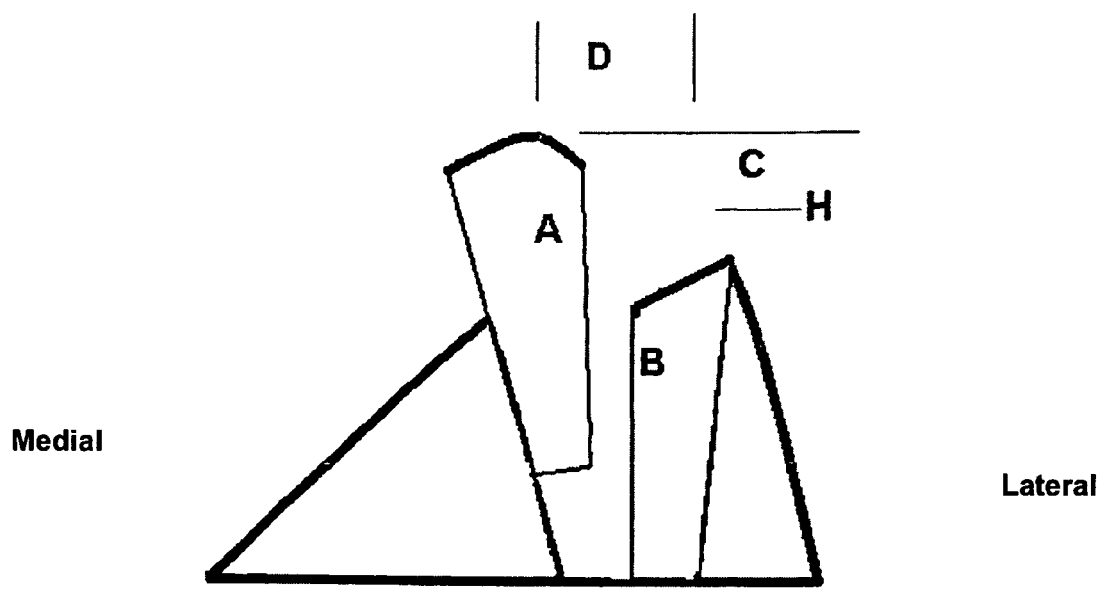
Figure 18:
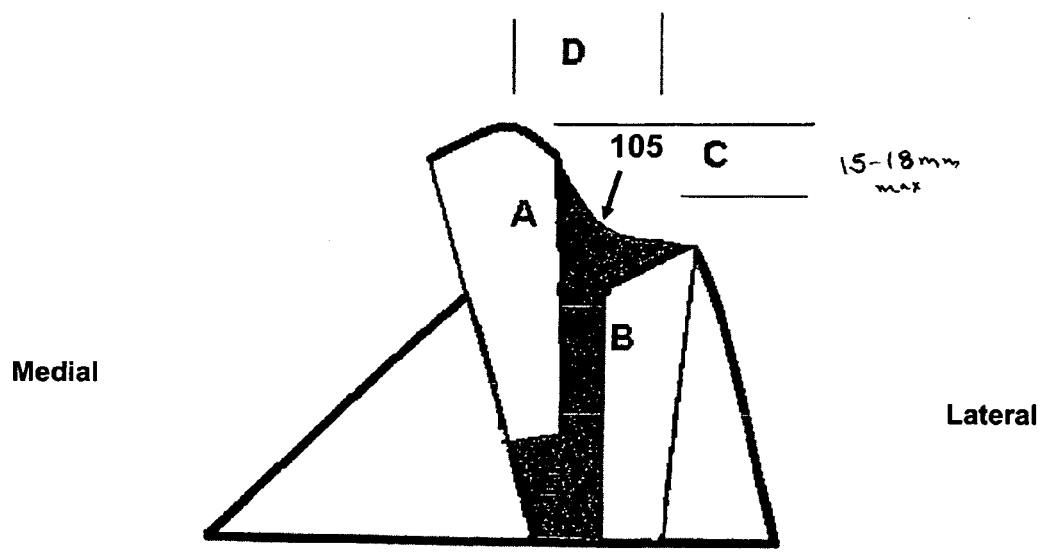
Figure 19:
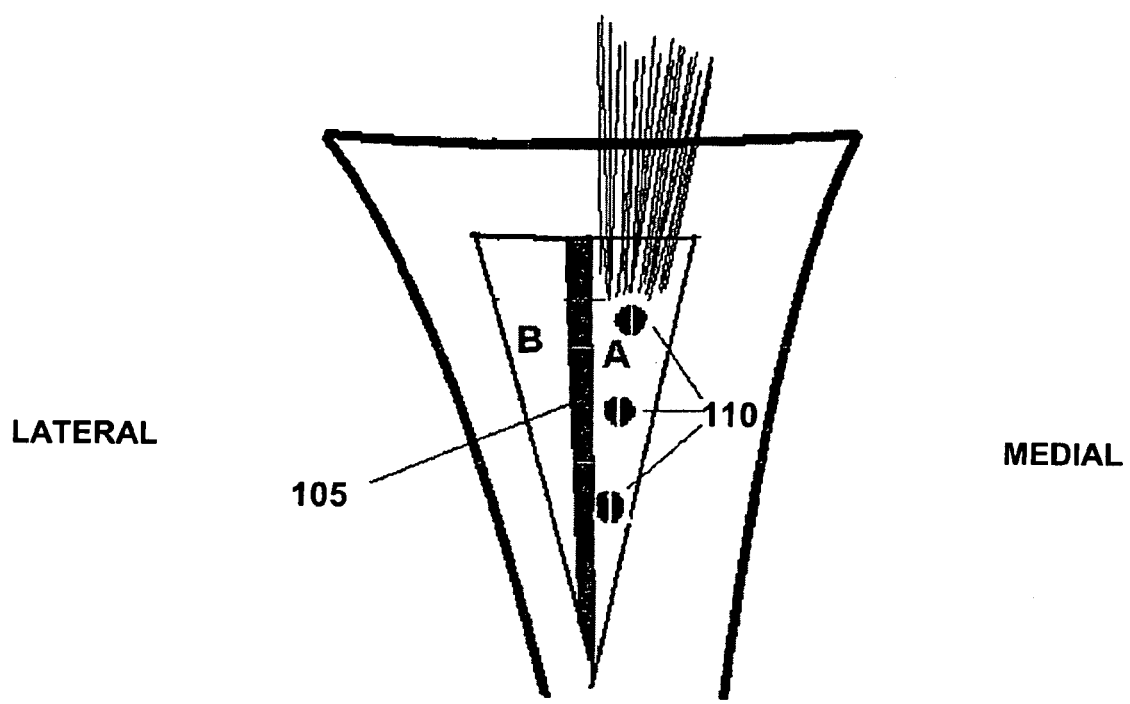
Figure 20:
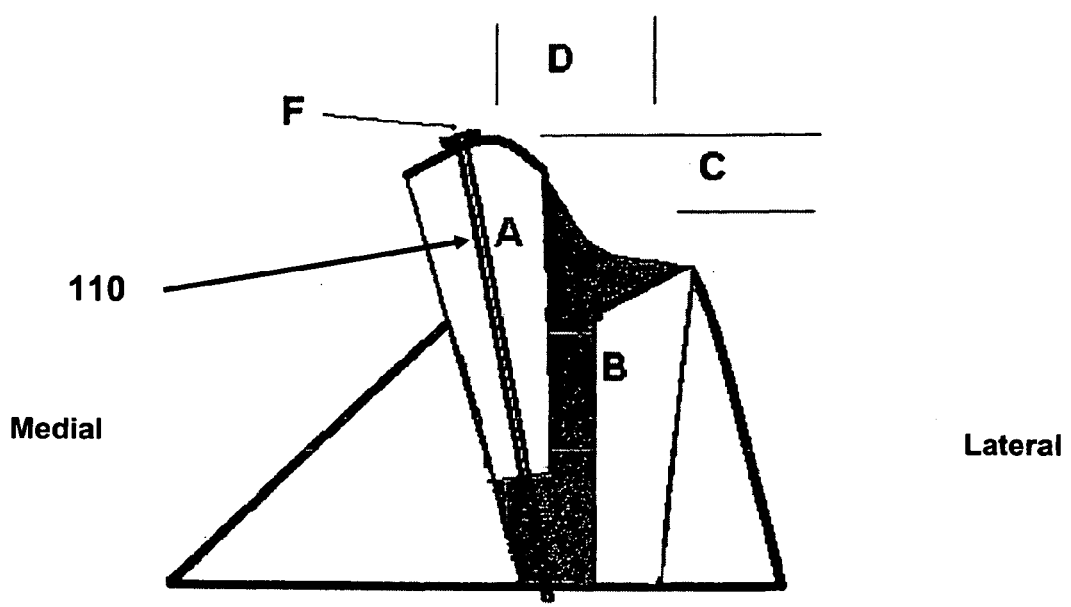
Figure 21:
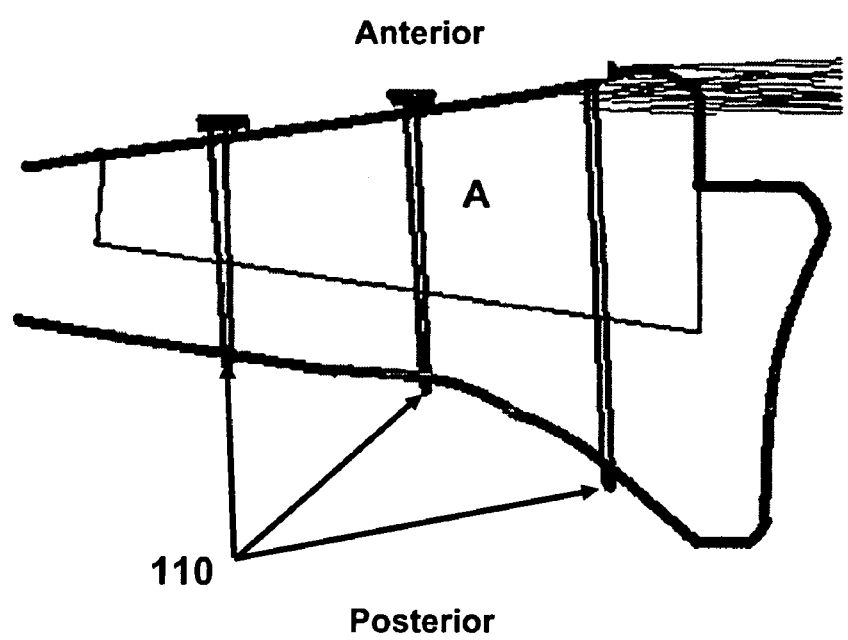
Figure 22:
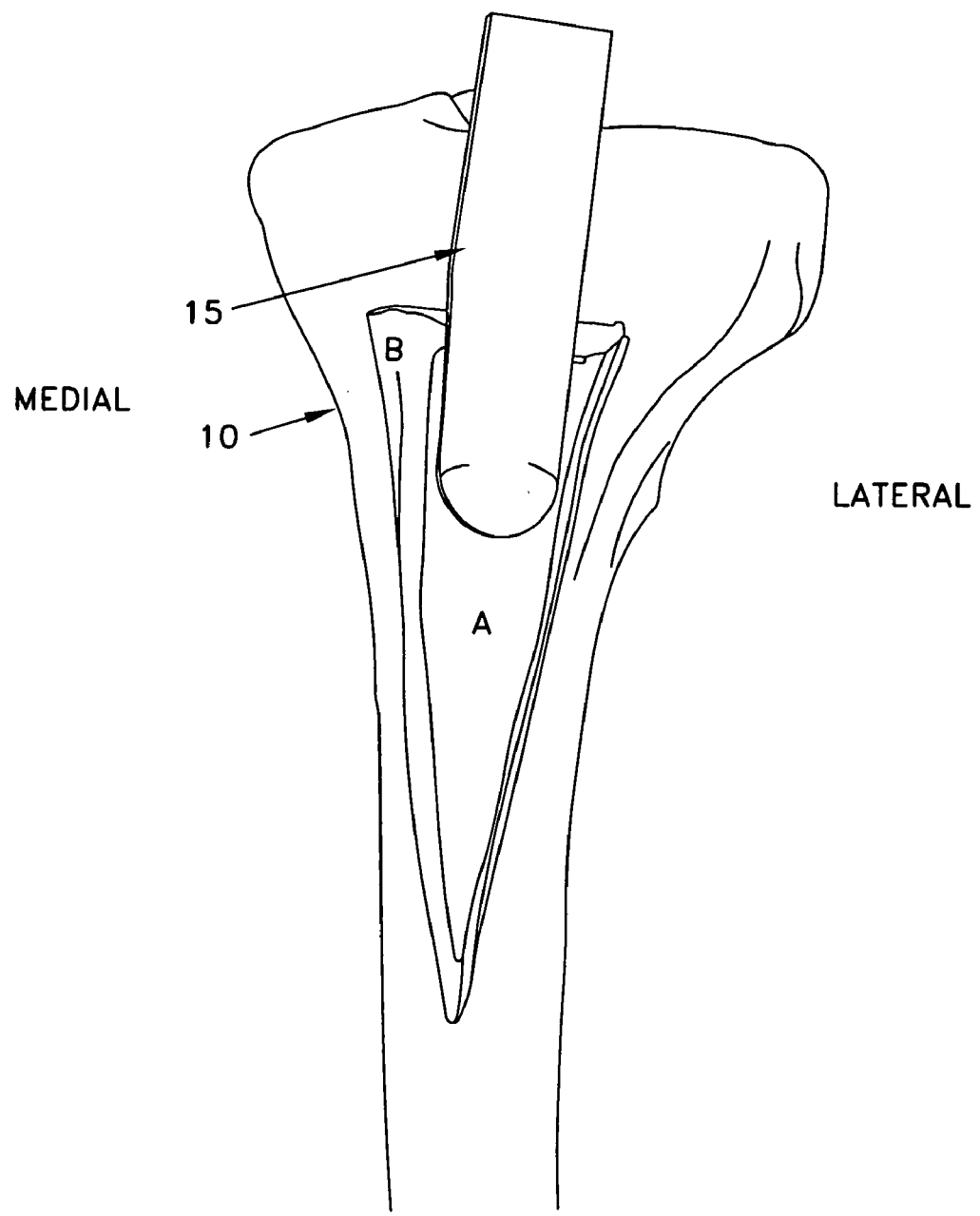
FIGS. 22-26 are a series of photographs showing the tibial tubercle transfer procedure being conducted on "saw bones"
Figure 23:
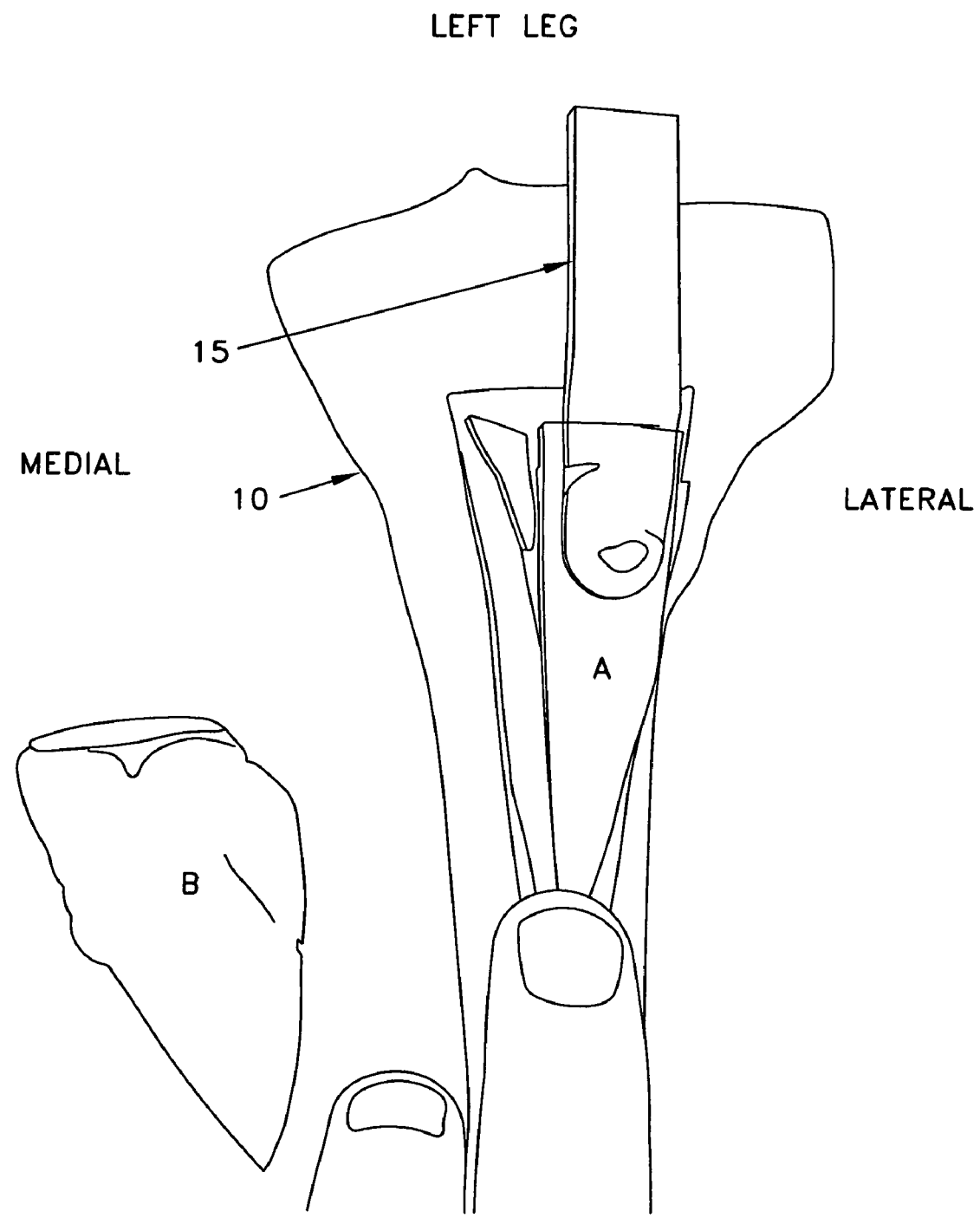
Figure 24:
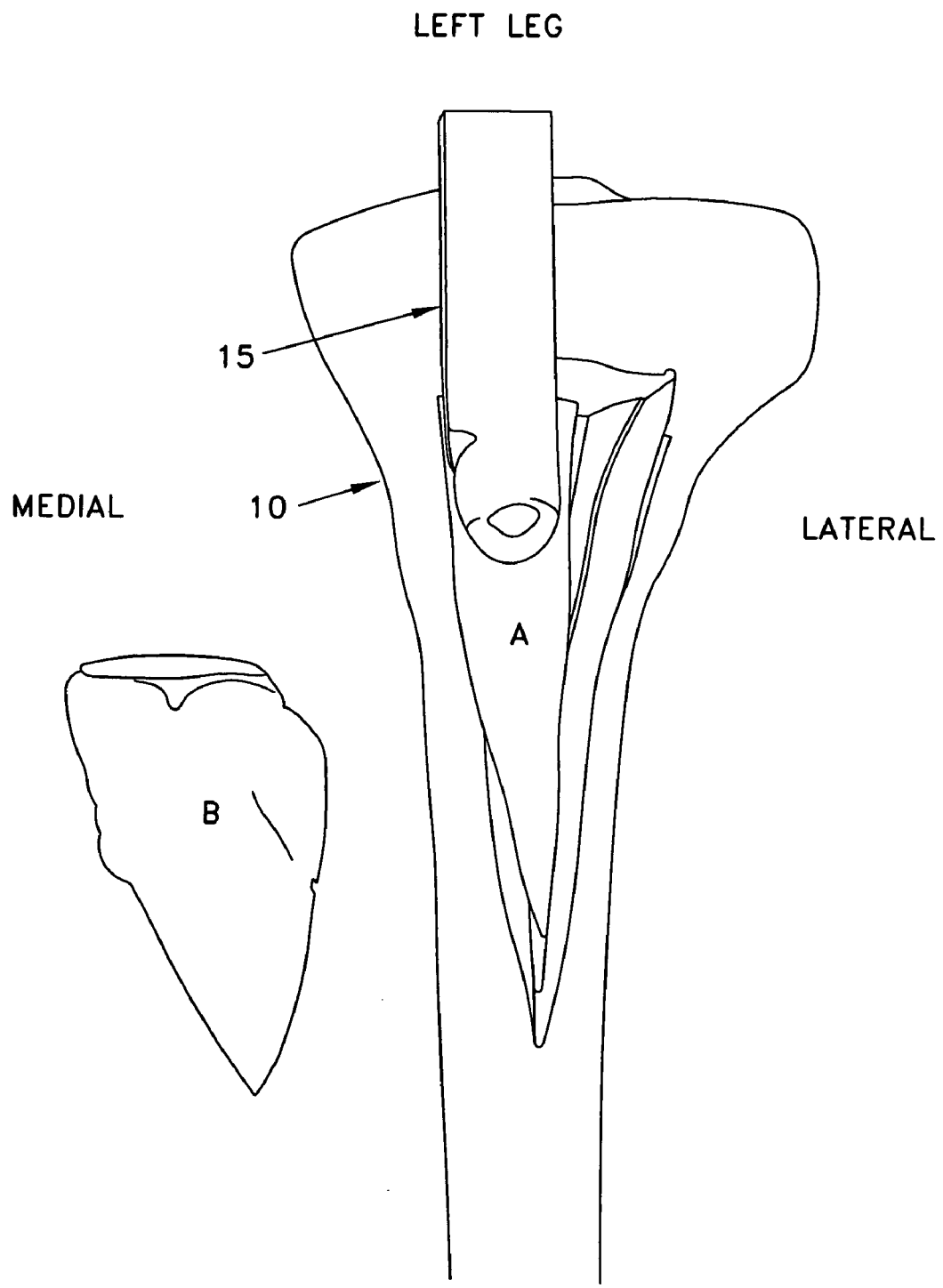
Figure 25:
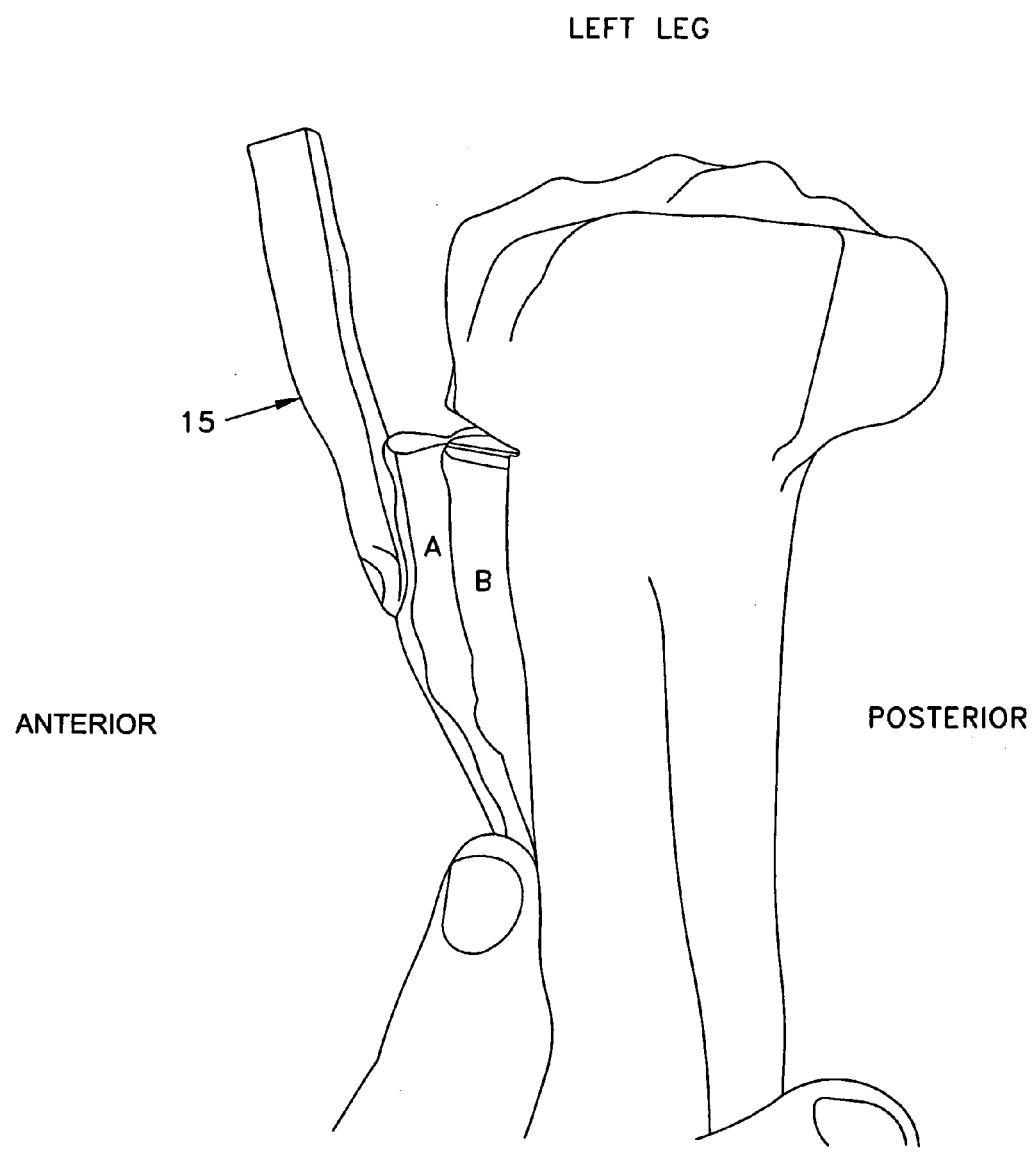
Figure 26:
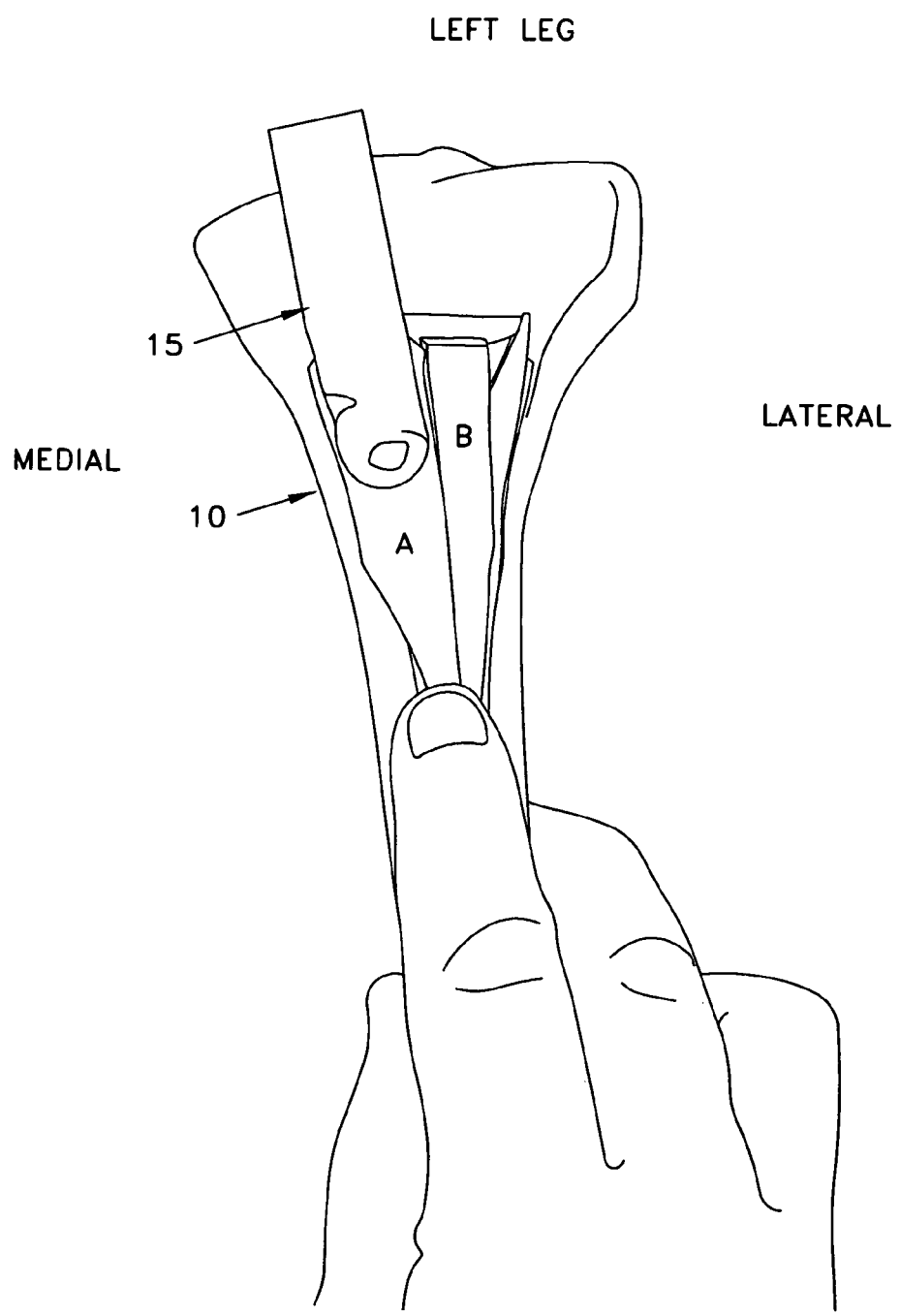

Thus, at this point in the procedure, two somewhat doubly-wedge-shaped (i.e., in a proximal-to-distal sense and in an anterior-to-posterior sense) blocks of bone A and B (FIGS. 13 and 14) have been created, with bone block A having the patellar tendon attached to it, and with bone block B sitting medial to bone block A.

By exchanging the side-by-side positioning of bone blocks A and B, the tibial tubercle (and patellar tendon) may be transferred medially.

More particularly, and looking now at FIGS. 12-21, the positions of the wedge-shaped bone blocks A and B are exchanged by (i) removing bone block A from tibia 10, (ii) transferring bone block B laterally, and (iii) inserting bone block A back into tibia 10, medially of bone block B. Alternatively, bone block B can be removed from the tibia, bone block A shifted laterally, and then bone block B inserted back into the tibia. To achieve a tight fit, and to compensate for the bone lost in the saw kerfs, bone graft material 105 can be inserted into tibia 10, medially and laterally of, and between, bone blocks A and B. Furthermore, as bone block A is inserted back into tibia 10, the anterior-posterior position of bone block A may be adjusted. More particularly, if anterior transfer of the tibial tubercle is desired, additional bone graft material can be inserted posterior to the transferred tibial tubercle bone block, thereby anteriorly advancing the tibial tubercle bone block the desired distance. Finally, the transferred tibial tubercle is fixed in its new position using multiple bone screws 110, i.e., bone blocks A and B are secured in position using a plurality of bone screws. Alternatively, and/or additionally, the transferred tibial tubercle may be fixed in its new position using bone cement.

See also FIGS. 22-26, which are a series of photographs showing the tibial tubercle transfer procedure being conducted on "saw bones".

Among other things, by adjusting the positioning of jig 25 and transverse cuts 75 and 100, distally or proximally, transfer of the tibial tubercle can be achieved as well.

Furthermore, adjustable sidearm 85 is preferably designed to be attached to either side of jig 25 so as to accommodate right or left knees. This approach also allows the device to be used for the relatively rare lateral tibial tubercle transfer, e.g., when revising an over-medialized previous tibial tubercle transfer.

Preferred Method and Apparatus for Effecting Tibial Tubercle Transfer

The following section builds upon and further teaches an improved, more precisely controllable, multidirectional, and independently variable tibial tubercle transfer technique. The invention is intended to be used in performing a patellar tendon re-alignment by moving the tibial tubercle medially, antero-medially, laterally, anterolaterally, distally, antero-distally, proximally, antero-proximally, or any combination thereof appropriate for a specific patient.

Several factors are important to performing an ideal, anatomically-preferred tibial tubercle transfer: (a) the surgeon should be able to move the tubercle wedge (into which the patellar tendon is inserted) a precise distance medially or laterally, etc., and (b) the surgeon should be able to move the tubercle wedge a precise distance anteriorly. The present invention provides the surgeon with instrumentation in the form of cutting guides that attach to the tibial tubercle and allow the surgeon to make precise cuts into the tibia with oscillating saw blades and osteotomes. The bone wedges produced by these cuts may then be precisely and accurately transposed within the tibia so as to re-align the patellar tendon laterally or medially and, if desired, the wedge associated with the patellar tendon insertion may be positioned anteriorly.

The novel method and apparatus of the present invention will be apparent from the following description of the preferred procedure to effect the tibial tubercle transfer. In this respect it should be appreciated that the preferred method and apparatus which will hereinafter be discussed is substantially the same as the method and apparatus discussed above and shown in FIGS. 1-26, except: the aforementioned jig 25 is replaced by a base jig 25A, and the aforementioned sidearm 85 is replaced by a polyetheretherketone (PEEK) shim 85A, wherein the PEEK shim 85A mounts to the base jig 25A with a tongue-and-groove construction, as will hereinafter be discussed.

Step 1. Make a longitudinal skin incision slightly lateral of midline, just lateral to the patellar tendon and tibial crest. Start the incision approximately 2 cm above the tubercle and extend distally for 6 cm.

Step 2. Dissect/release the subcutaneous tissues as required.

Step 3. Dissect the retro-patellar tendon space between the patellar tendon insertion (into the tibial tubercle) and the patella.

Figure 27:
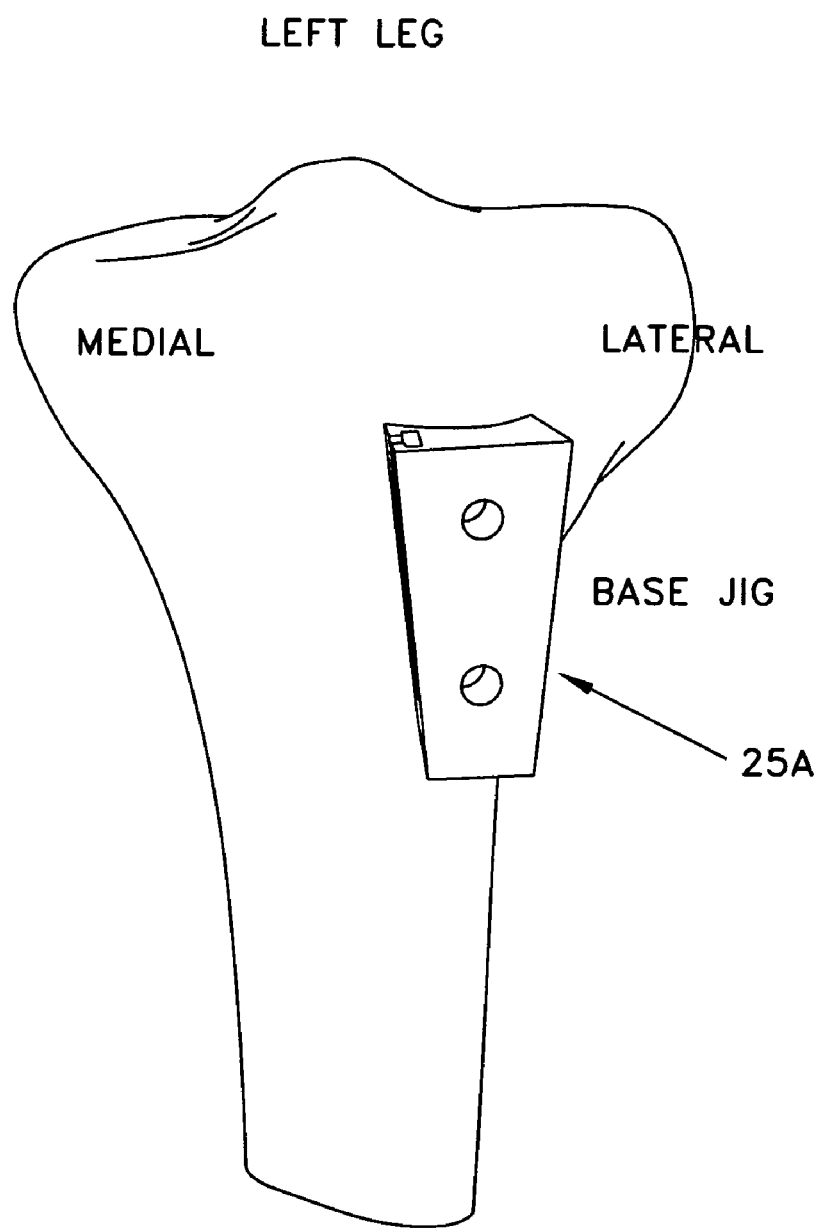
FIGS. 27-44 are a series of schematic views illustrating the preferred method and apparatus for effecting tibial tubercle transfer procedure.

Step 4. Position the base jig 25A on the tibial tubercle (FIG. 27). Base jig 25A is selected so as to be sized proportional to the size of the portion of the tibial tubercle which is to be transferred. To this end, the surgeon is preferably provided with a surgical kit comprising a plurality of various-sized base jigs for use with the tibial tubercle transfer procedure of the present invention. This allows the surgeon to select the appropriate base jig for use in a particular patient's procedure.

Figure 28:
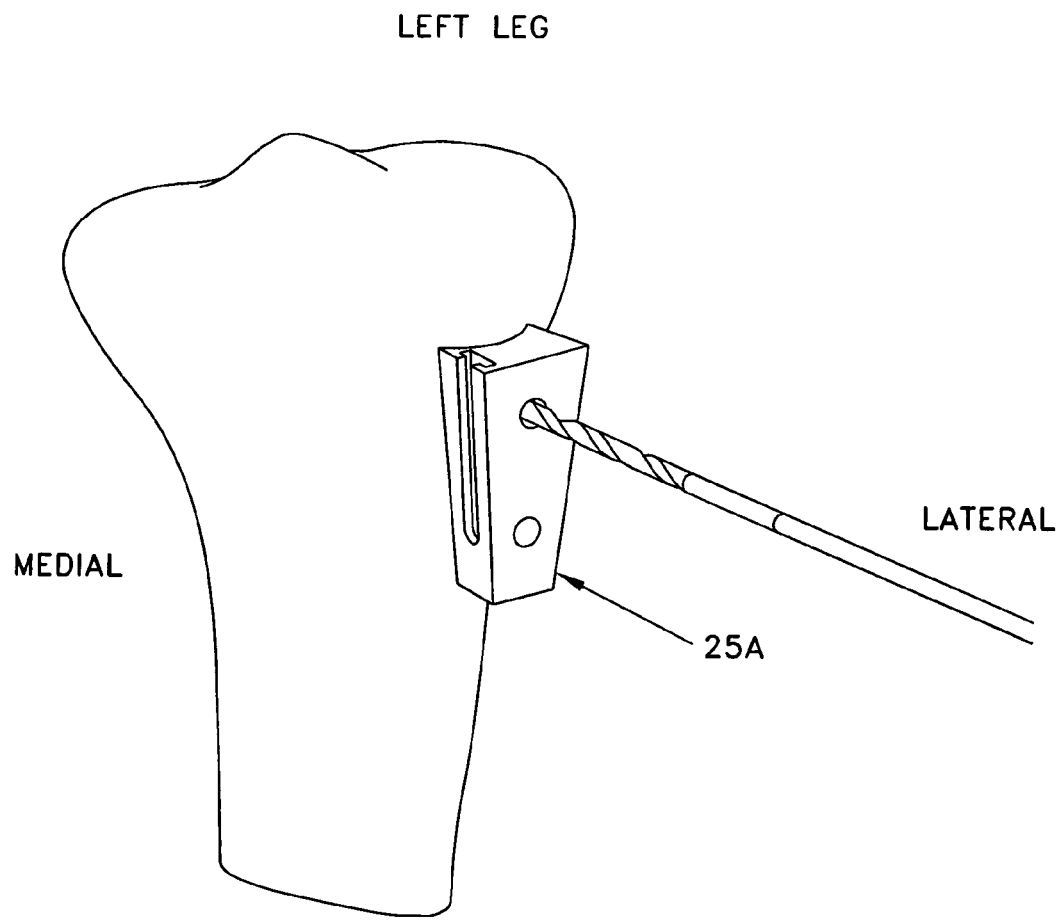
Figure 29:
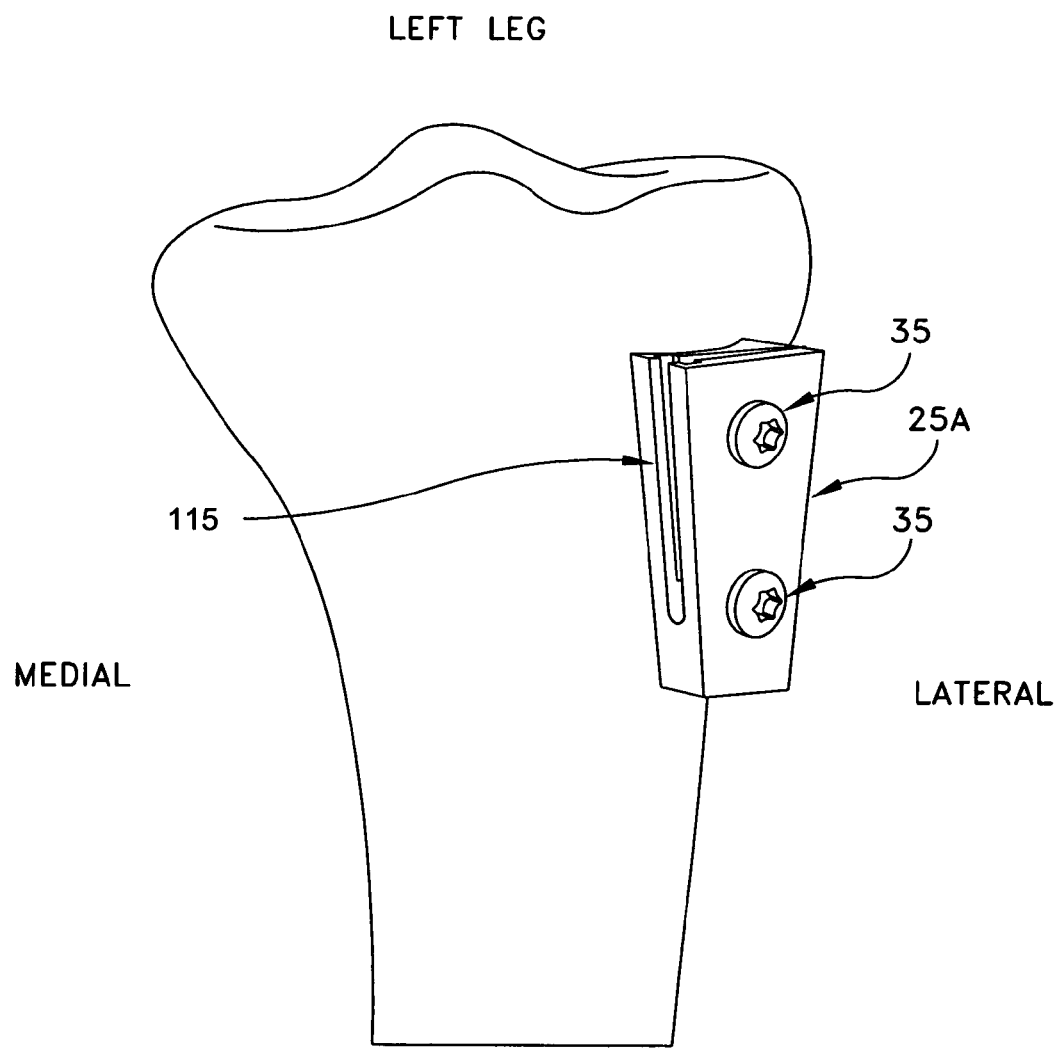

Step 5. Drill 3.2 mm diameter holes through the base jig 25A to 25 mm depth and fix the base jig 25A to the tibial tubercle 5 using 4.5 mm diameter, 28 mm long thread-cutting cortical bone screws 35 (FIGS. 28 and 29).

Figure 30:
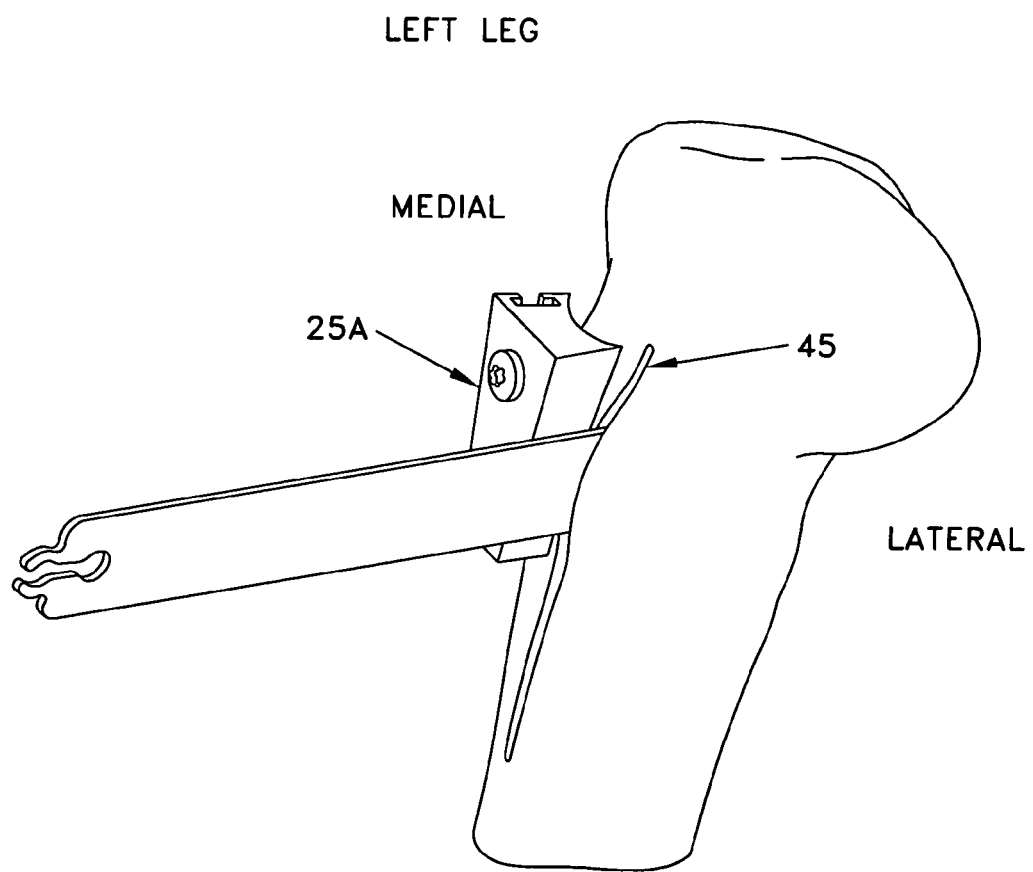
Figure 31:
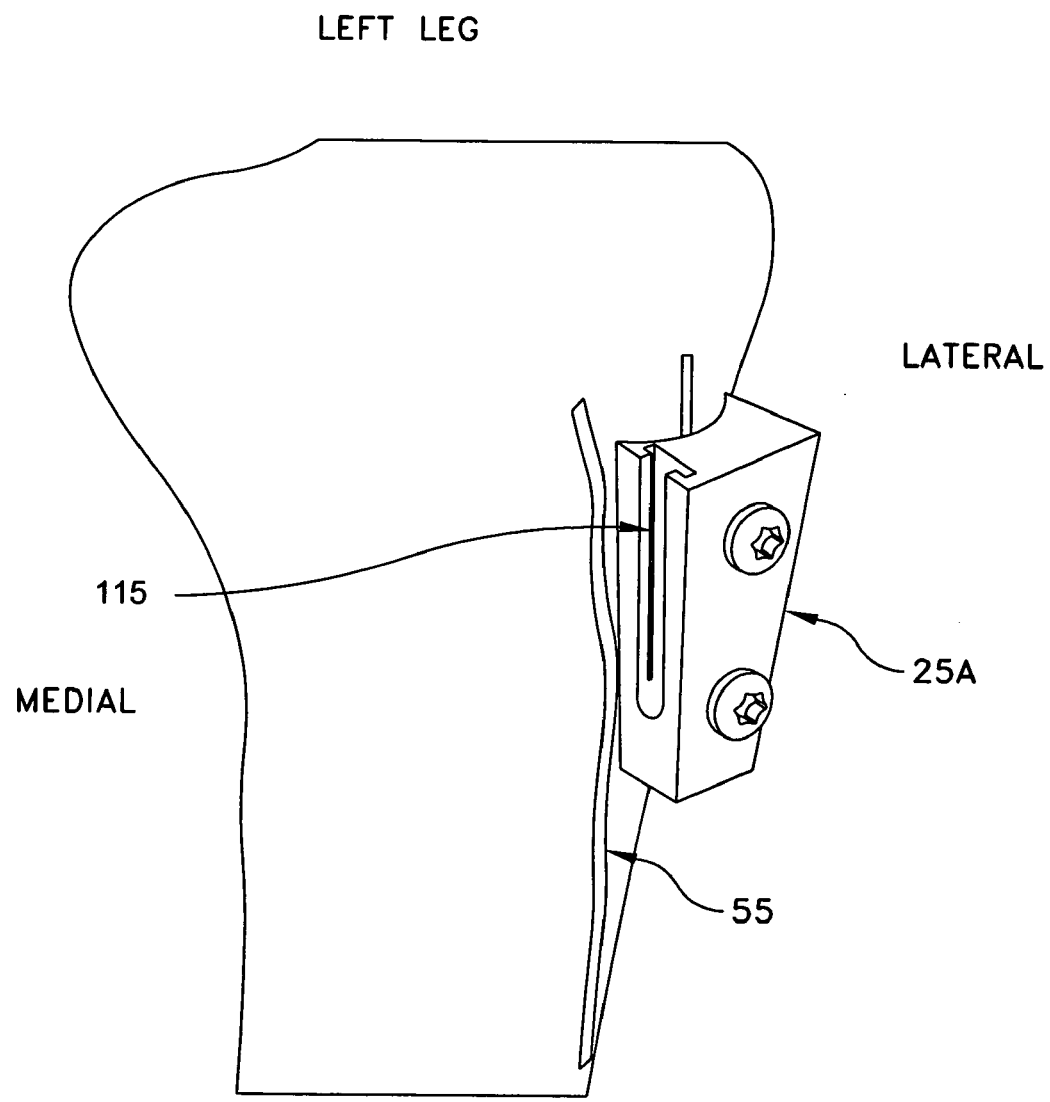

Step 6. Holding a broad face 0.9 mm saw blade flush against the lateral and medial faces of base jig 25A, create bone block A by making the lateral and medial longitudinal cuts 45, 55 through the cortical bone, extending the cuts inferiorly beneath the skin until the two cuts intersect (FIGS. 30 and 31).

Step 7. Using a thin (0.9 mm) non-tapered osteotome, deepen the cuts to the posterior cortex (FIG. 32) to complete bone block A.

Figure 32:
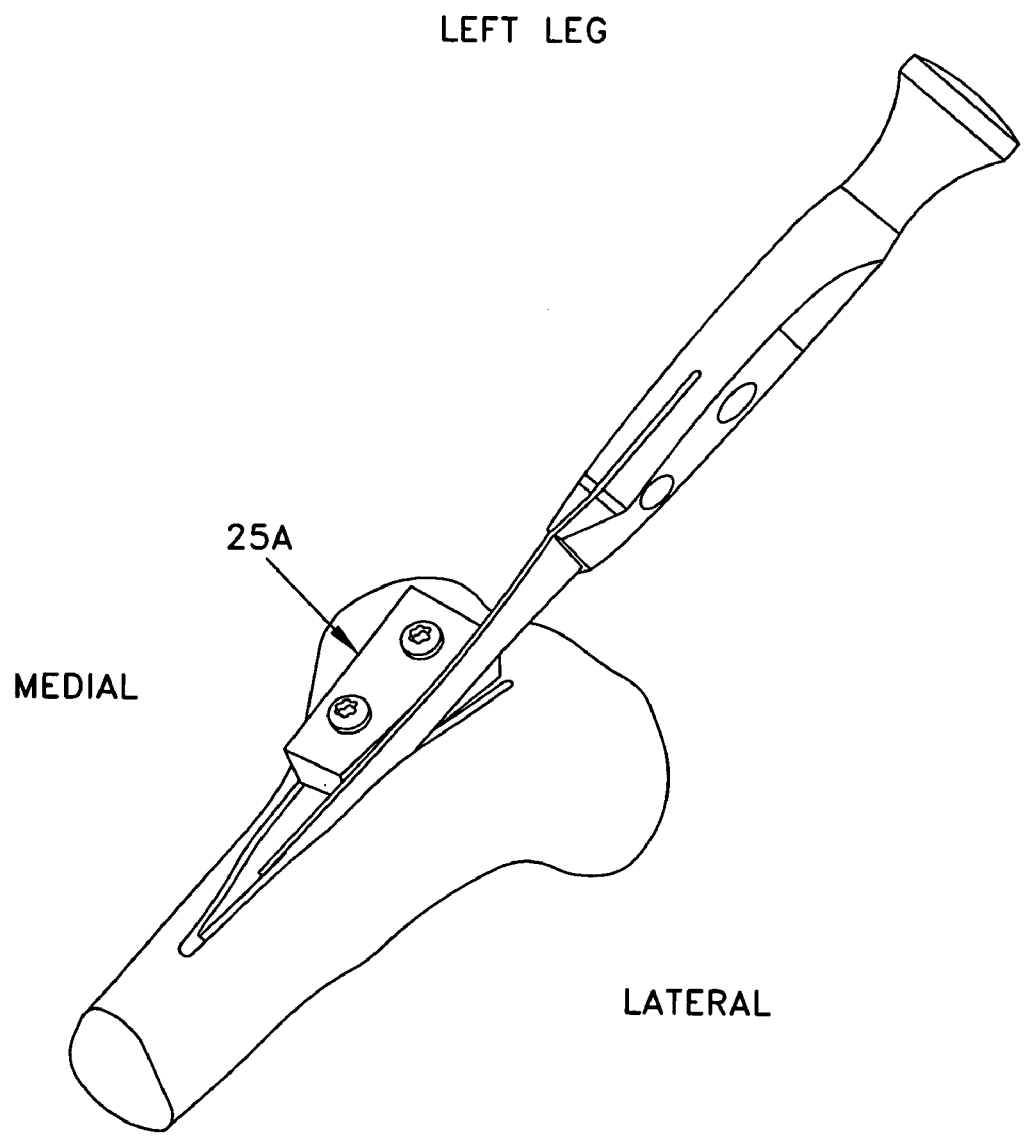
Figure 33:
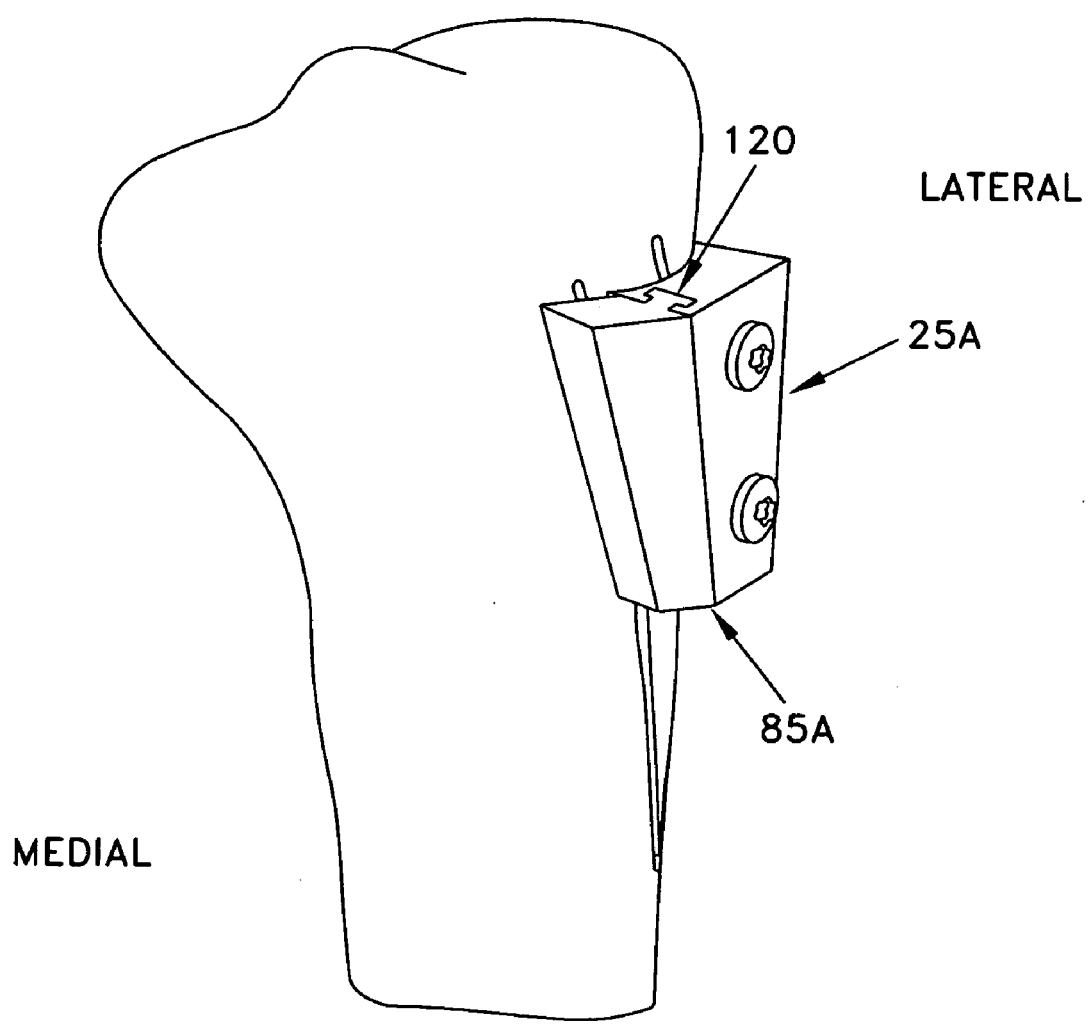

Step 8. Insert the PEEK shim 85A into the base jig 25A (FIG. 32). In one preferred form of the invention, this is done by inserting the tongue 115 of PEEK shim 85A into the groove 120 of base jig 25A. Alternatively, PEEK shim 85A may be provided with the groove 115, and base jig 25A may be provided with the tongue 120. Furthermore, it should also be appreciated that PEEK shim 85A may be fixed to base jig 25A using other means, e.g., by screwing, by press-fitting, etc. PEEK shim 85A is sized in accordance with the desired medialization or lateralization increment. To this end, the surgeon is preferably provided with a surgical kit comprising a plurality of various-sized PEEK shims for use with the tibial tubercle transfer procedure of the present invention. This allows the surgeon to select the appropriate PEEK shim for use in a particular patient's procedure.

Figure 34:
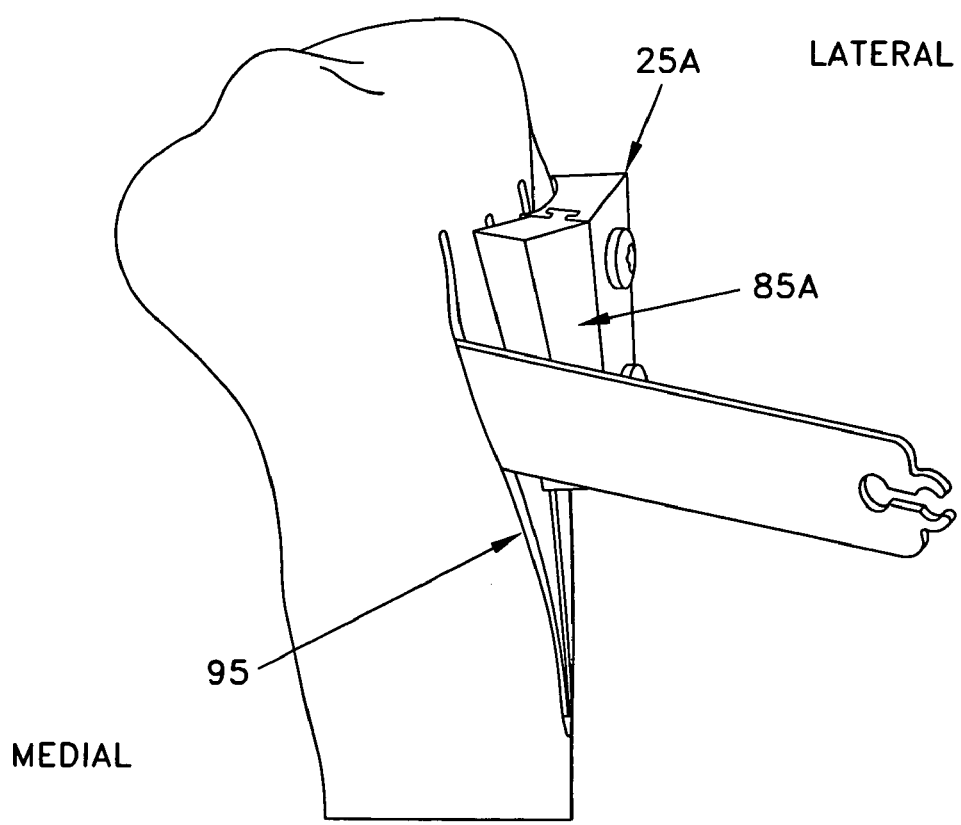

Step 9. Create bone block B by making a third longitudinal cut 95 using the thin saw and osteotomes as in Steps 6 and 7, intersecting the previous two cuts inferiorly at their apex (FIG. 34).

Figure 35:
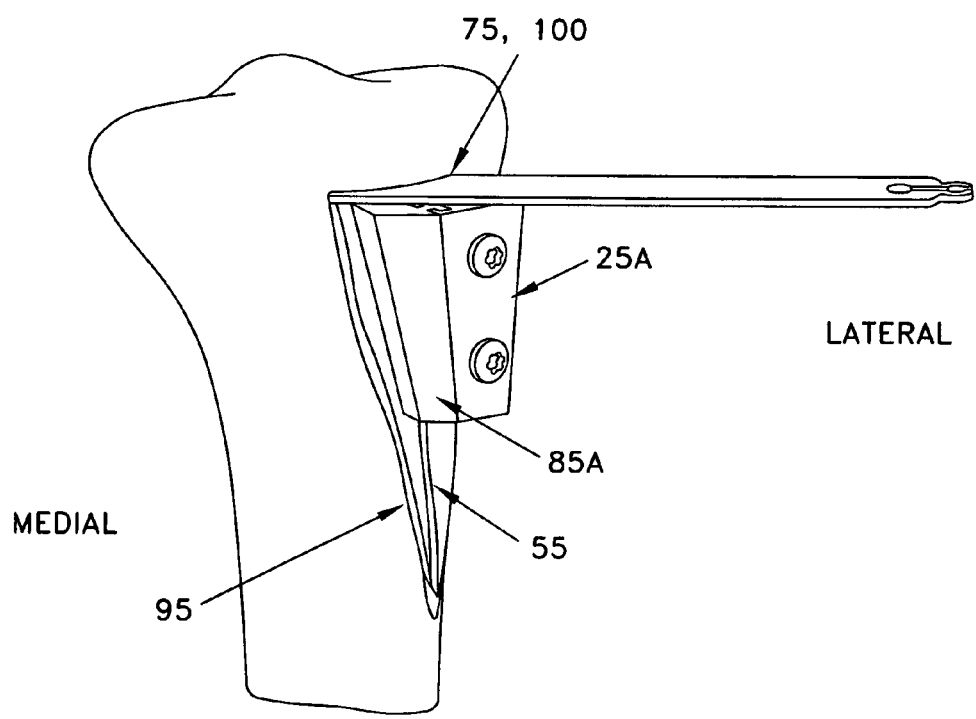

Step 10. Make a transverse cut 75, 100 posterior to the patellar tendon using the superior faces of the base jig 25A and PEEK shim 85A as the cutting guides to complete the two wedges forming bone blocks A and B (FIG. 35).

Figure 36:
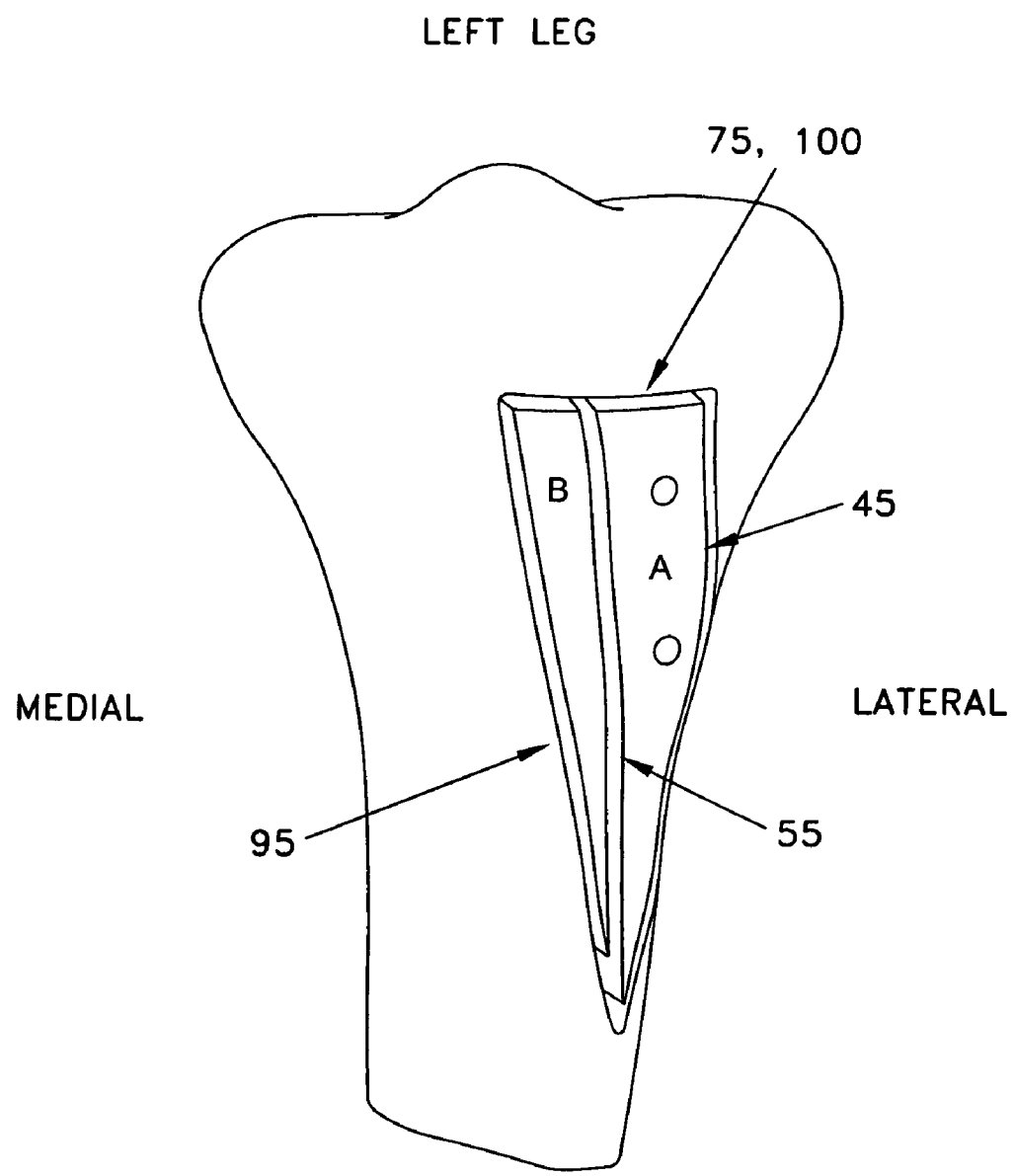
Figure 37:
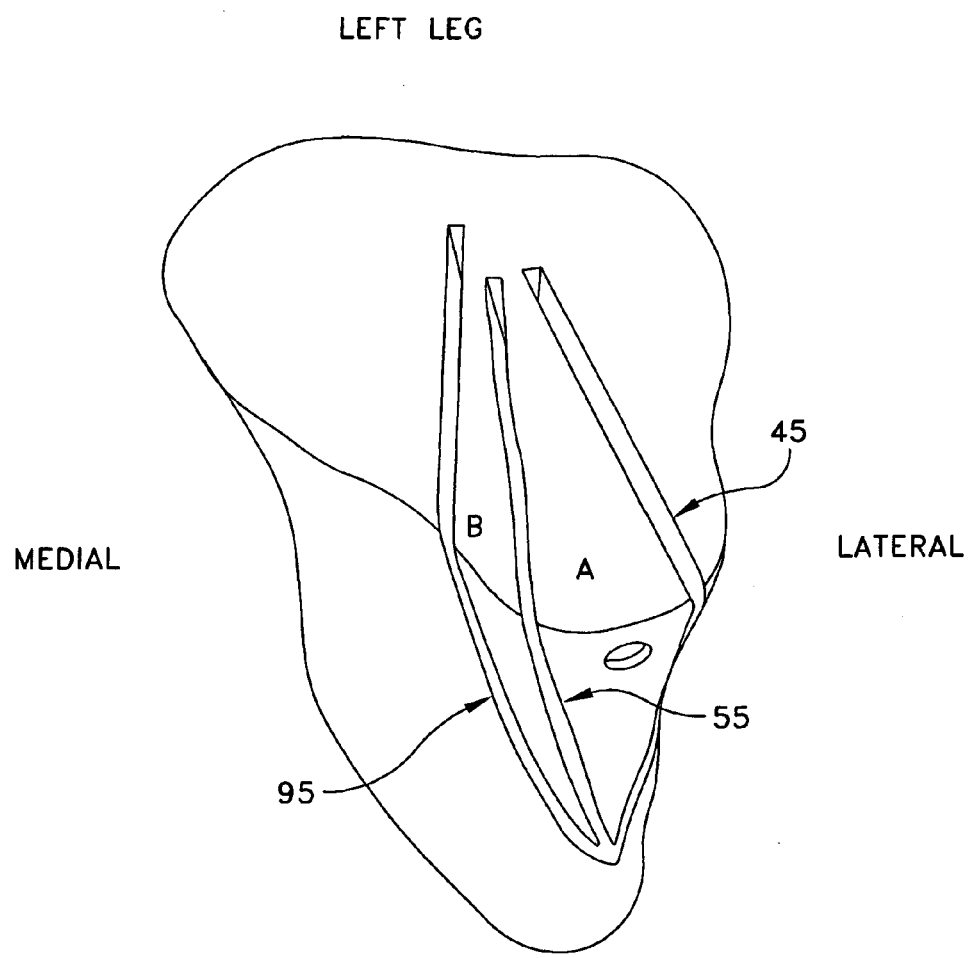

Step 11. Remove the PEEK shim 85A from the base jig 25A. FIGS. 36 and 37 show frontal and section views of the tibia after the four cuts have been completed.

Step 12. Release the wedges from their attachments by applying appropriate hand or finger force.

Figure 38:
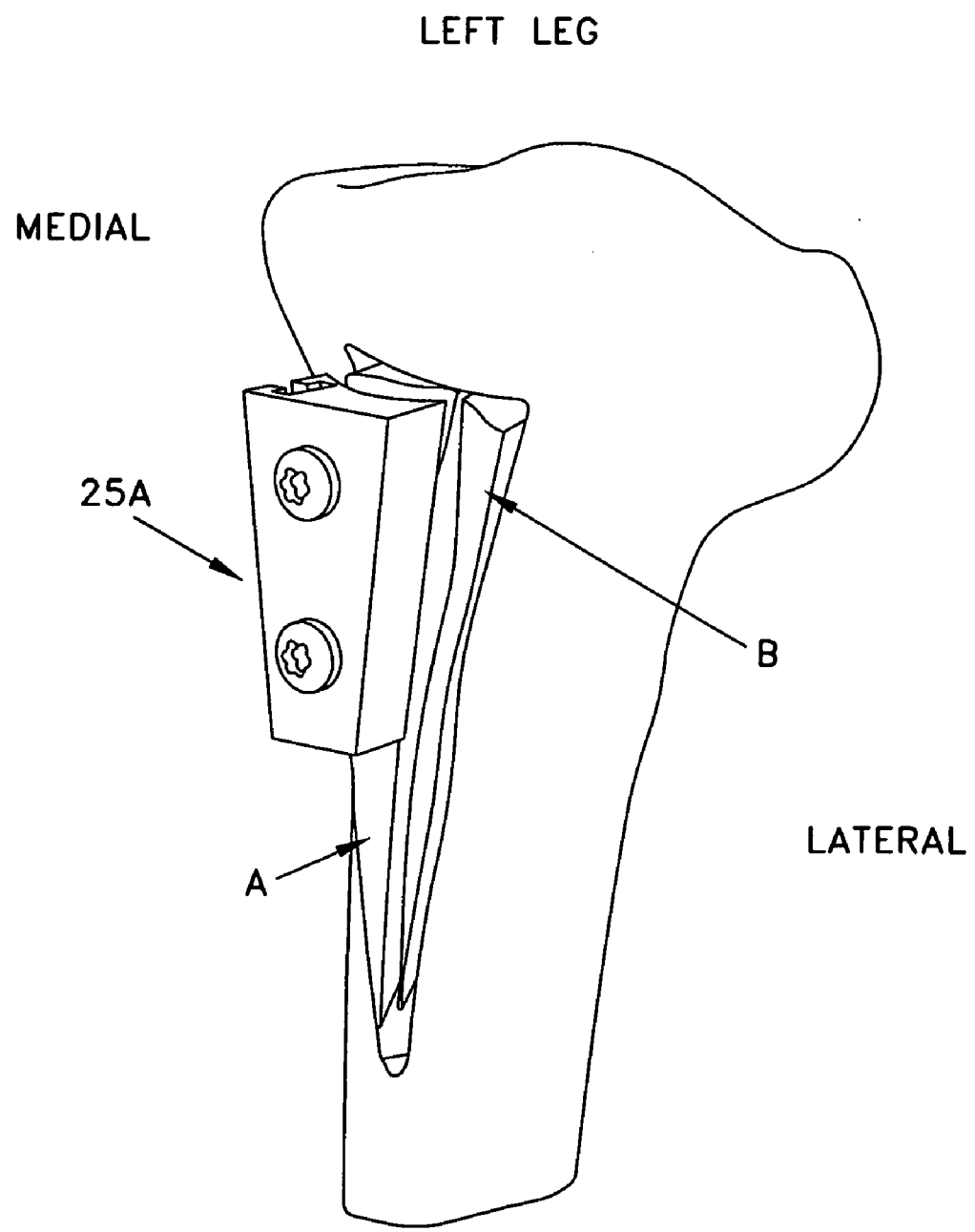

Step 13. Lift out and transpose the cut wedges to move the tibial tubercle into the medial position (FIG. 38).

Step 14. Pack bone graft material 105 into the spaces between and around the bone wedges as needed. If anteriorization is desired, pack bone graft material 105 behind the bone block A to create the correct degree of anterior wedge displacement.

Step 15. Measure the Q-angle intra-operatively to assure the desired correction.

Step 16. Unscrew and remove the distal cortical bone screw 35 from the base jig 25A.

Figure 39:
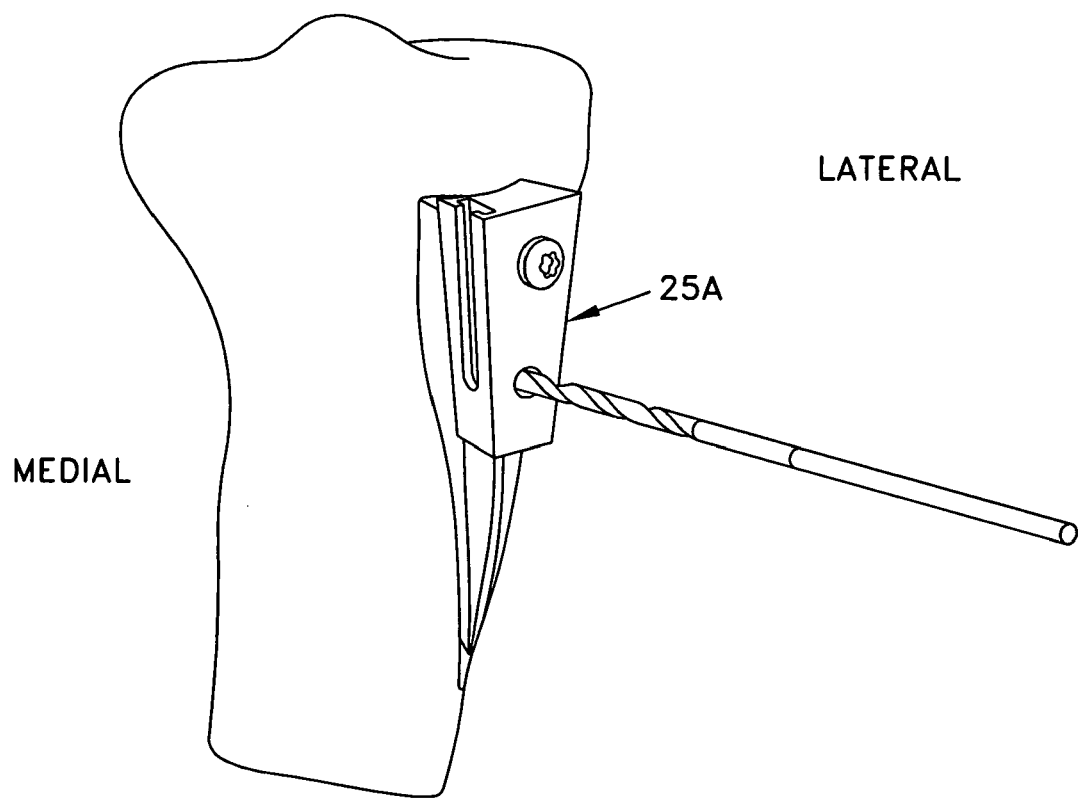

Step 17. Holding the tibial tubercle 5 in its new position, drill a 3.2 mm diameter pilot hole through the distal hole in the base jig and through the posterior cortex using care, with the knee flexed (FIG. 39).

Step 18. Remove the proximal bone screw 35 and remove the base jig 25A.

Step 19. Measure and select a fixation screw.

Figure 40:
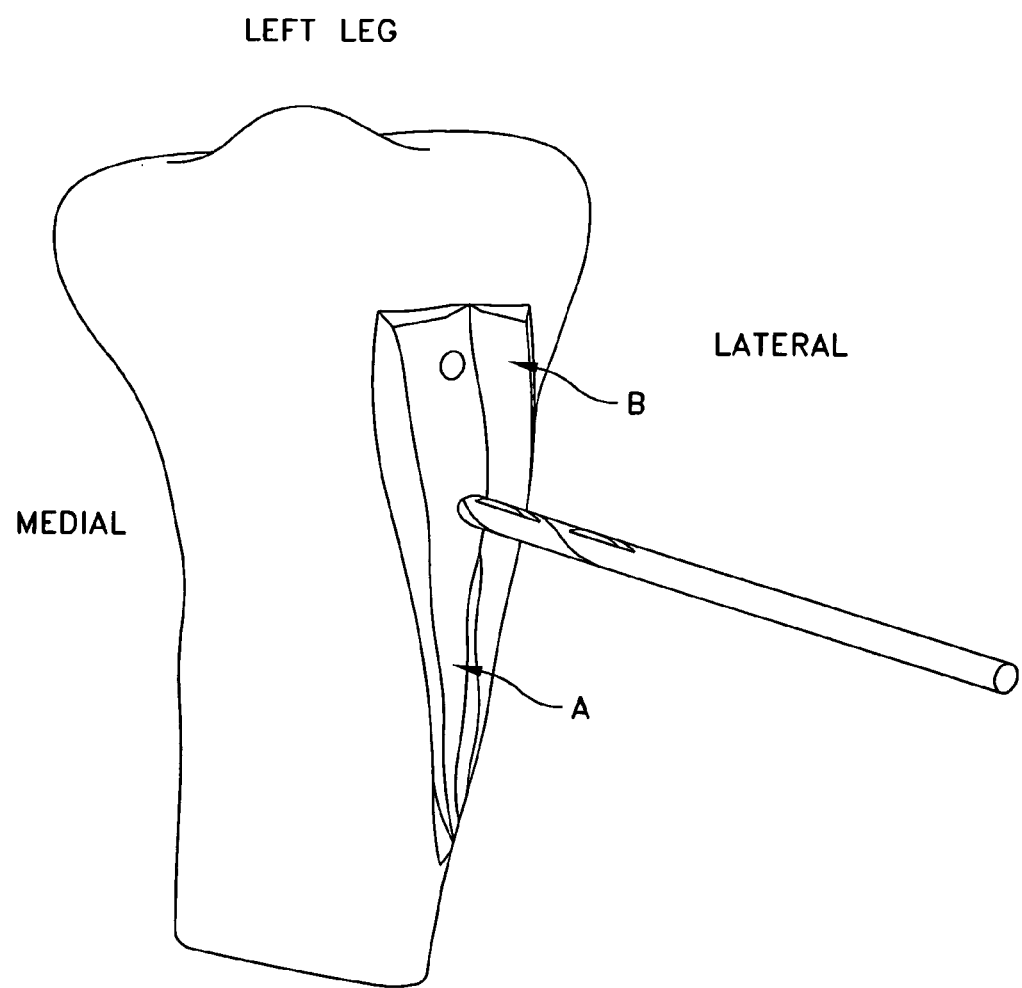

Step 20. Over-drill the distal tibial tubercle pilot hole a short distance with a 4.5 mm drill bit to create a thread lag (FIG. 40).

Figure 41:
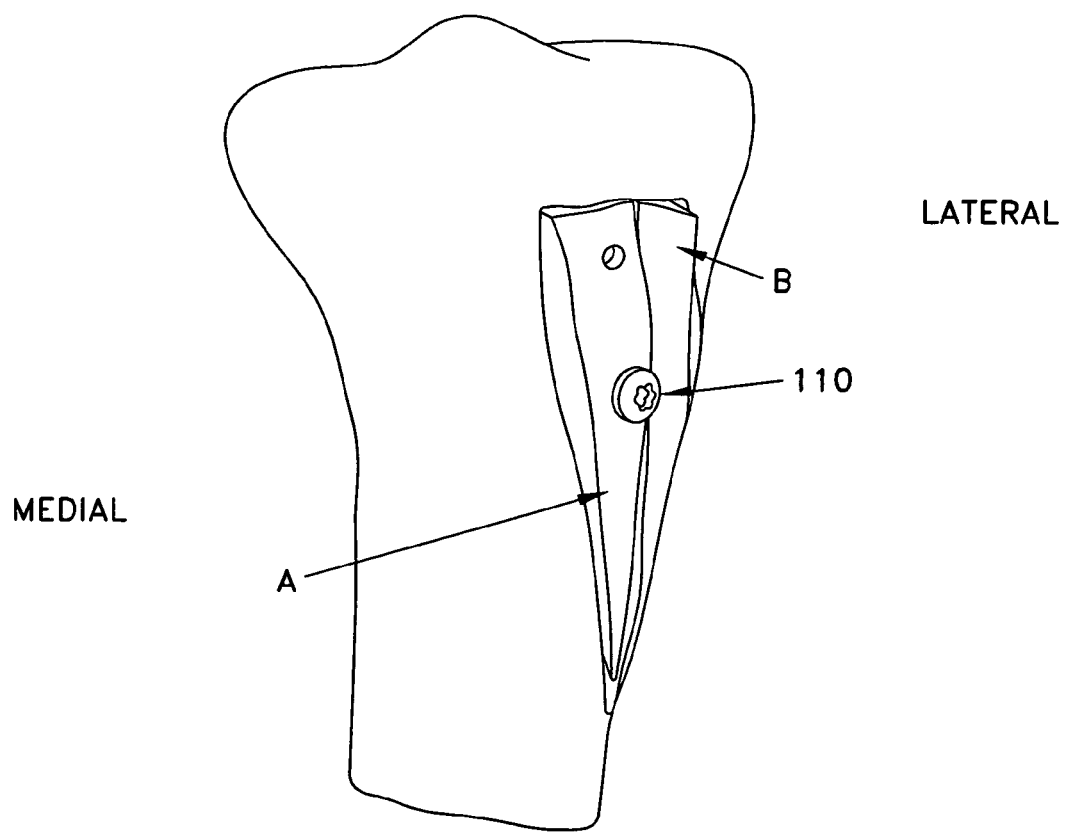

Step 21. Insert and secure the first (distal) fixation screw 110 (FIG. 41).

Figure 42:
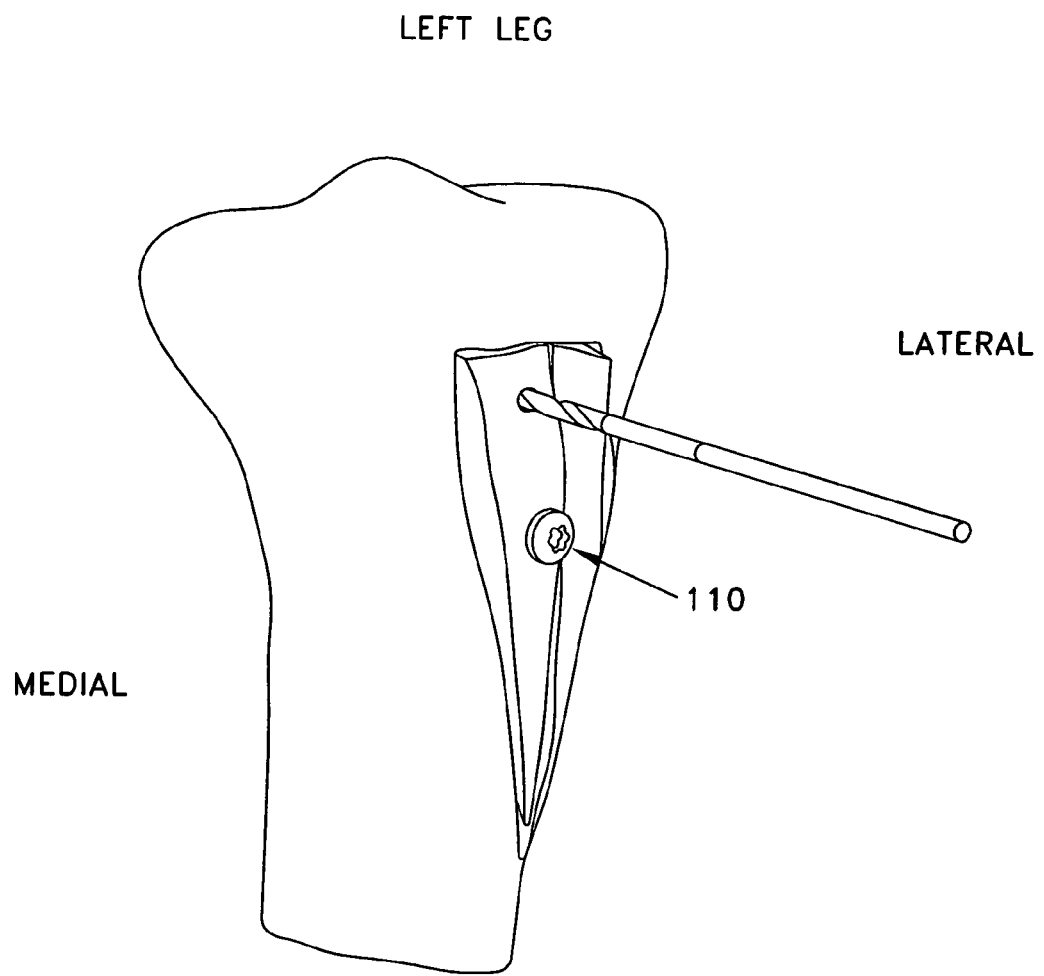
Figure 43:
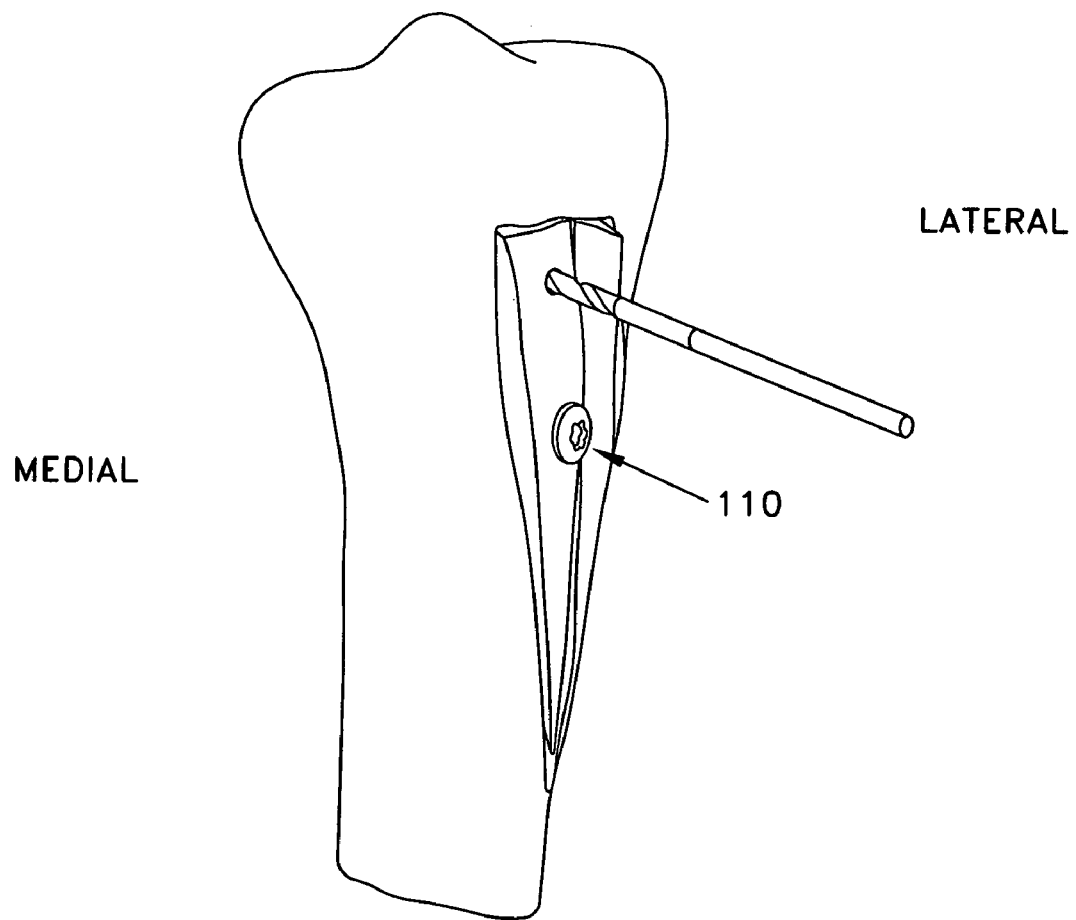
Figure 44:
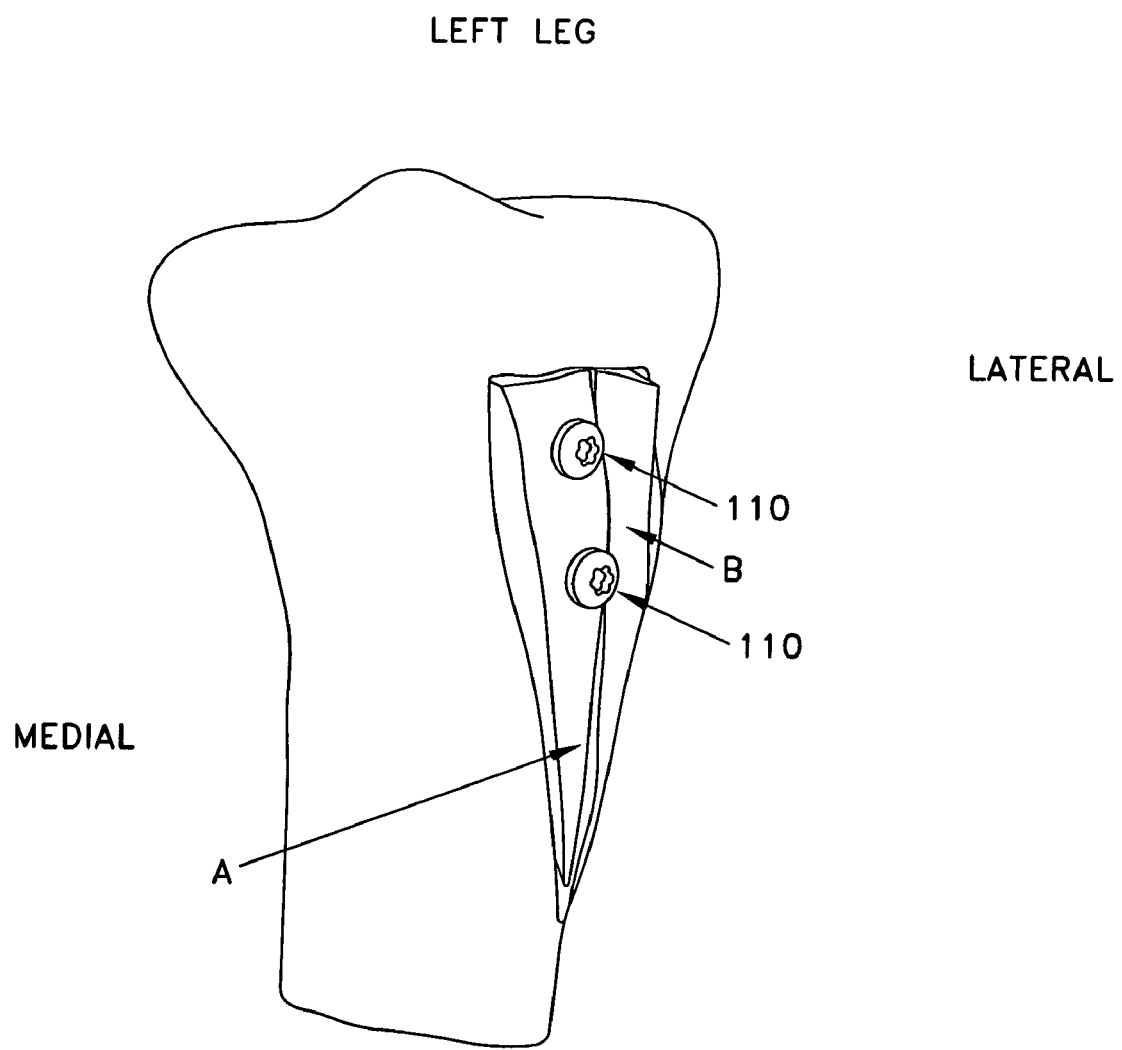

Step 22. Repeat Steps 17-21 for a fixation screw 110 in the proximal hole (FIGS. 42-44).

Step 23. [Optional] If a third fixation screw 110 is desired, drill a 3.2 mm pilot hole to the posterior cortex as above in the preferred location, over-drill the pilot hole with a 4.5 mm drill a short distance to create a thread lag, and insert the appropriate length cortical bone screw.

Step 24. Alternatively, and/or additionally, the transferred tibial tubercle may be fixed in its new position using bone cement.

Modifications

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for performing a multidirectional tibial tubercle transfer, comprising:
    positioning a jig against the anterior portion of the tibia, the jig comprising first and second cutting guides, wherein the first and second cutting guides simultaneously converge towards one another as they extend (i) distally down the tibia, and (ii) posteriorly towards the tibia;
    cutting first and second saw cuts into the tibia, wherein the first saw cut is aligned with the first cutting guide and the second saw cut is aligned with the second cutting guide;
    attaching an extender to the jig, wherein the extender comprises a third cutting guide, wherein the third cutting guide simultaneously converges towards the first cutting guide as the third cutting guide extends (i) distally down the tibia, and (ii) posteriorly towards the tibia;

cutting a third saw cut into the tibia, wherein the third saw cut is aligned with the third cutting guide;

freeing a first bone block from the tibia, wherein the first bone block is formed between the first saw cut and the second saw cut, and freeing a second bone block from the tibia, wherein the second bone block is formed between the first saw cut and the third saw cut; and transferring the position of the first bone block relative to the tibia.

2. A method according to claim 1 wherein transferring the position of the first bone block relative to the tibia comprises moving the first bone block medially.

3. A method according to claim 1 further comprising adjusting the anterior-posterior position of the first bone block relative to the tibia.

4. A method according to claim 1 wherein transferring the position of the first bone block relative to the tibia comprises switching the positions of the first and second bone blocks relative to one another.

5. A method according to claim 1 wherein the jig comprises a transverse cutting guide, wherein the transverse cutting guide extends perpendicular to the longitudinal axis of the tibia, and further wherein the method comprises cutting a transverse saw cut into the tibia.

6. A method according to claim 1 wherein the lateral extender comprises a transverse cutting guide, wherein the transverse cutting guide extends perpendicular to the longitudinal axis of the tibia, and further wherein the method comprises cutting a transverse saw cut into the tibia.

7. A method according to claim 1 wherein the extender comprises a sidearm adjustably mounted to the jig.

8. A method according to claim 1 wherein the extender comprises a shim detachably mounted to the jig.

9. A method according to claim 8 wherein the jig comprises at least one of a tongue-and-groove connection, and wherein the shim comprises the other of the tongue-and-groove connection.

10. A method according to claim 1 further comprising securing the first bone block to the tibia with at least one screw.

11. A method according to claim 1 further comprising securing the second bone block to the tibia with at least one screw.

12. A method according to claim 1 further comprising positioning bone graft material adjacent to the first bone block.

13. Apparatus for performing a multidirectional tibial tubercle transfer, comprising:

a jig for positioning against the anterior portion of the tibia, the jig comprising first and second cutting guides, wherein the first and second cutting guides simultaneously converge towards one another as they extend (i) distally down the tibia, and (ii) posteriorly towards the tibia; and an extender for attaching to the jig, wherein the extender comprises a third cutting guide, wherein the third cutting guide simultaneously converges towards the first cutting guide as the third cutting guide extends (i) distally down the tibia, and (ii) posteriorly towards the tibia.

14. Apparatus according to claim 13 wherein the size of the jig is determined by the size of the tibial tubercle.

15. Apparatus according to claim 13 wherein the size of the extender is determined by the extent to which the tibial tubercle is to be transferred.

16. Apparatus according to claim 13 wherein the jig and the extender are configured to move the first bone block medially.

17. Apparatus according to claim 13 wherein the jig comprises a transverse cutting guide, and wherein the transverse cutting guide extends perpendicular to the longitudinal axis of the tibia.

18. Apparatus according to claim 13 wherein the extender comprises a transverse cutting guide, and wherein the transverse cutting guide extends perpendicular to the longitudinal axis of the tibia.

19. Apparatus method according to claim 13 wherein the extender comprises a sidearm adjustably mounted to the jig.

20. Apparatus according to claim 13 wherein the extender comprises a shim detachably mounted to the jig.

21. Apparatus according to claim 13 wherein the jig comprises at least one of a tongue-and-groove connection, and wherein the shim comprises the other of the tongue-and-groove connection.

22. A method according to claim 1 further comprising securing the second bone block to the tibia with bone cement.

23. A method according to claim 1 further comprising securing the second bone block to the tibia with a bioabsorbable compound.

24. A method according to claim 1 wherein transferring the position of the first bone block relative to the tibia comprises moving the first bone block laterally.

25. Apparatus according to claim 13 wherein the jig and the extender are configured to move the first bone block laterally.

26. A method according to claim 1 wherein the jig is selected from a kit comprising a plurality of various-sized jigs.

27. Apparatus according to claim 13 wherein the jig is selected from a kit comprising a plurality of various-sized jigs.

* * * * *